US012042525B2

(12) United States Patent
Schwartz et al.

(10) Patent No.: US 12,042,525 B2
(45) Date of Patent: Jul. 23, 2024

(54) SERUM RESPONSE FACTOR REGENERATES SENESCENT CELLS

(71) Applicant: University of Houston System, Houston, TX (US)

(72) Inventors: Robert J. Schwartz, Houston, TX (US); Dinakar Iyer, Houston, TX (US)

(73) Assignee: University of Houston System, Houston, TX (US)

( * ) Notice: Subject to any disclaimer, the term of this patent is extended or adjusted under 35 U.S.C. 154(b) by 1052 days.

(21) Appl. No.: 16/959,944

(22) PCT Filed: Dec. 31, 2018

(86) PCT No.: PCT/US2018/068203
§ 371 (c)(1),
(2) Date: Jul. 2, 2020

(87) PCT Pub. No.: WO2019/136031
PCT Pub. Date: Jul. 11, 2019

(65) Prior Publication Data

US 2021/0069294 A1 Mar. 11, 2021

Related U.S. Application Data

(60) Provisional application No. 62/614,190, filed on Jan. 5, 2018.

(51) Int. Cl.

*A61K 38/17* (2006.01)
*A61K 45/06* (2006.01)
*A61K 47/69* (2017.01)
*C12N 15/86* (2006.01)

(52) U.S. Cl.

CPC ...... *A61K 38/1709* (2013.01); *A61K 47/6929* (2017.08); *C12N 15/86* (2013.01); *A61K 45/06* (2013.01)

(58) Field of Classification Search

CPC ............ A61K 38/1709; A61K 47/6292; A61K 45/06; A61P 9/04; C07K 2319/10; C07K 14/4702; C12N 15/86; C12N 2501/60; C12N 2506/1307; C12N 5/0657; C12N 2506/1315

USPC .......... 514/44 R, 44 A; 435/6.1, 91.1, 91.31, 435/455, 458; 536/23.1, 24.5

See application file for complete search history.

(56) References Cited

U.S. PATENT DOCUMENTS

2005/0037961 A1 2/2005 Schwartz et al.
2009/0187998 A1 7/2009 Wei et al.
2010/0008891 A1 1/2010 Webb et al.
2012/0213738 A1 8/2012 Nam et al.

FOREIGN PATENT DOCUMENTS

EP 3431593 1/2019
WO WO 2004/064763 8/2004
WO WO 2017/159463 9/2017

OTHER PUBLICATIONS

Belaguli et al., "Cardiac tissue enriched factors serum response factor and GATA-4 are mutual coregulators," *Mol. Cell. Biol.*, 20(20):7550-7558, 2000.

Belaguli et al., "Dominant negative murine serum response factor: alternative splicing within the activation domain inhibits transactivation of serum response factor binding targets," *Molecular and Cellular Biology*, 19(7):4582-4591, 1999.

Beltrami et al., "Adult cardiac stem cells are multipotent and support myocardial regeneration," *Cell*, 114:763-776, 2003.

Budniatzky et al., "Concise review: reprogramming strategies for cardiovascular regenerative medicine: from induced pluripotent stem cells to direct reprogramming," *Stem Cells Translational Medicine*, 3:448-457, 2014.

Cen et al., "Megakaryoblastic leukemia 1, a potent transcriptional coactivator for serum response factor (SRF), is required for serum induction of SRF target genes," *Mol.Cell. Biol*, 23(18):6597-6608, 2003.

Chong et al., "Human embryonic-stem-cell-derived cardiomyocytes regenerate non-human primate hearts," *Nature*, 510:273-277, 2014.

Christoforou et al., "Transcription factors MYOCD, SRF, Mesp1 and SMARCD3 enhance the cardio-inducing effect of GATA4, TBX5, and MEF2C during direct cellular reprogramming," *PLoS One*, 8(5):e63577, 2013.

Dierickx et al., "Embryonic template-based generation and purification of pluripotent stem cell-derived cardiomyocytes for heart repair," *Journal of Cardiovascular Translational Research*, 5(5):566-580, 2012.

Extended European Search Report issued in European Application No. 18898014.8, mailed Sep. 23, 2021.

(Continued)

*Primary Examiner* — Jane J Zara

(74) *Attorney, Agent, or Firm* — Parker Highlander PLLC

(57) ABSTRACT

Loss of cardiomyocytes underlies most causes of heart failure, and normal repair processes are inadequate to deal with extensive myocardial damage. The inventors have identified mutations of the N-terminus of serum response factor (SRF)'s MADS box, termed STEMINs, that block cardiac differentiation, but also powerfully activate the stem cell marker genes Nanog and Octomer 4, as well as cyclins, which promotes adult myocyte replication. SRF Stemin mutations are not cardiac-specific, and also propel mammalian fibroblasts into a proliferative state. Thus, STEMINs may be useful for regeneration of all tissue and organ types, by activating partial pluripotency programs and enhancing repair by increased cell replication. Following withdrawal of STEMINs, the cells then return to normal cell identity.

19 Claims, 6 Drawing Sheets

Specification includes a Sequence Listing.

(56) References Cited

OTHER PUBLICATIONS

Gupta et al., "Physical interaction between the MADS box of serum response factor and the TEA/ATTS DNA-binding domain of transcription enhancer factor-1," *The Journal of Biological Chemistry*, 276(13):10413-10422, 2001.

Hare et al., "Comparison of allogeneic vs autologous bone marrow-derived mesenchymal stem cells delivered by transendocardial injection in patients with ischemic cardiomyopathy: the POSEIDON randomized trial," *JAMA*, 308:2369-2379, 2012.

Laflamme et al., "Cardiomyocytes derived from human embryonic stem cells in pro-survival factors enhance function of infarcted rat hearts," *Nat. Biotechnol.*, 25:1015-1024, 2007.

Murry et al., "Regeneration gaps: observations on stem cells and cardiac repair," *J Am Coll Cardiol*, 47:1777-1785, 2006.

Niu et al., "Serum response factor orchestrates nascent sarcomerogenesis and silences the biomineralization gene program in the heart," *Proc Natl Acad Sci U S A*, 105(46):17824-17829, 2008.

PCT International Search Report and Written Opinion issued in International Application No. PCT/US2018/068203, mailed May 1, 2019.

Sepulveda et al., "Combinatorial expression of GATA4, Nkx2-5, and serum response factor directs early cardiac gene activity," *J. Biol. Chem.*, 277:25775-25782, 2002.

Travers et al., "Cardiac fibrosis—the fibroblast awakens," *Circulation Research*, 118(6):1021-1040, 2016.

Wang et al., "Activation of cardiac gene expression by myocardin, a transcriptional cofactor for serum response factor," *Cell*, 105:851-862, 2001.

Wang et al., "Myocardin and ternary complex factors compete for SRF to control smooth muscle gene expression," *Nature*, 428:185-189, 2004.

Xiao et al., "STEMIN and YAP5SA synthetic modified mRNAs regenerate and repair infarcted mouse hearts", *J. Cardiovasc Aging*, 2:31, 2022.

Xiao et al., "Mutant SFR and YAP synthetic modified mRNAs drive cardiomyocyte nuclear replication", *J. Cardiovasc Aging*, vol. 2, 2022.

Zhang et al., "Functional cardiomyocytes derived from human induced pluripotent stem cells," *Circ Res.*, 104:e30-e41, 2009.

N-extension α1

140aa 150aa

```
          PGKKTRGRVKIKMEFIDNKL-
141(A3)   PGKKTAAAVKIKMEFIDNKL-
144(A3)   PGKKTRGRAAAKMEFIDNKL-
147(A3)   PGKKTRGRVKIAAAFIDNKL-
150(A3)   PGKKTRGRVKIKMEAAANKL-
153(A3)   PGKKTRGRVKIKMEFIDAAA-
```

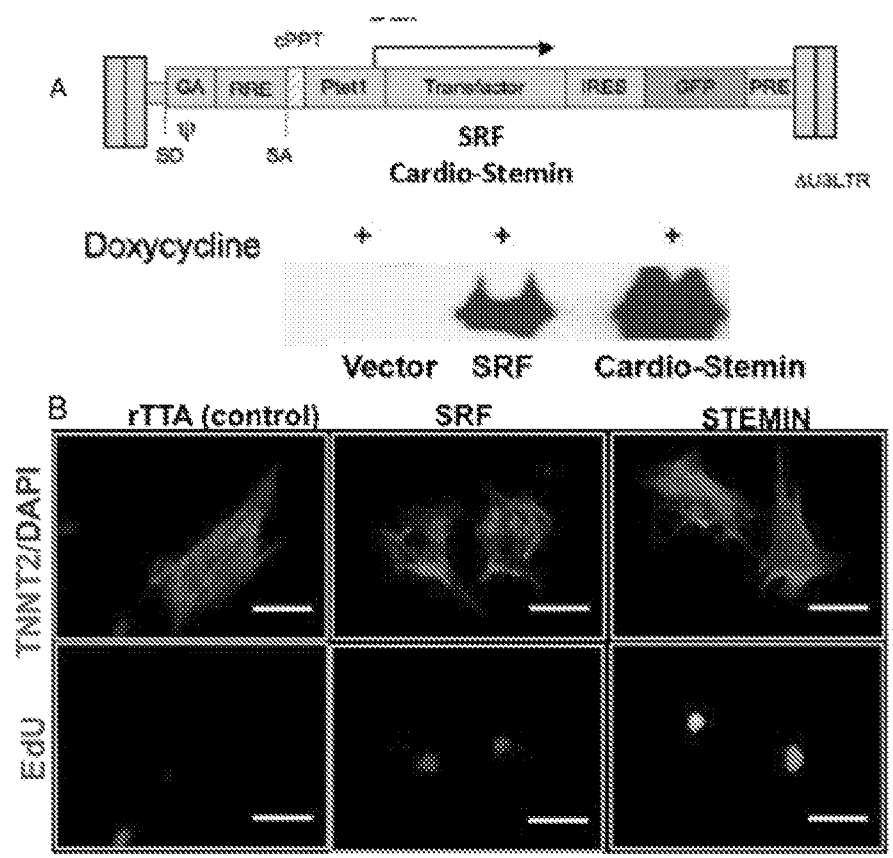
FIGS. 6A-B
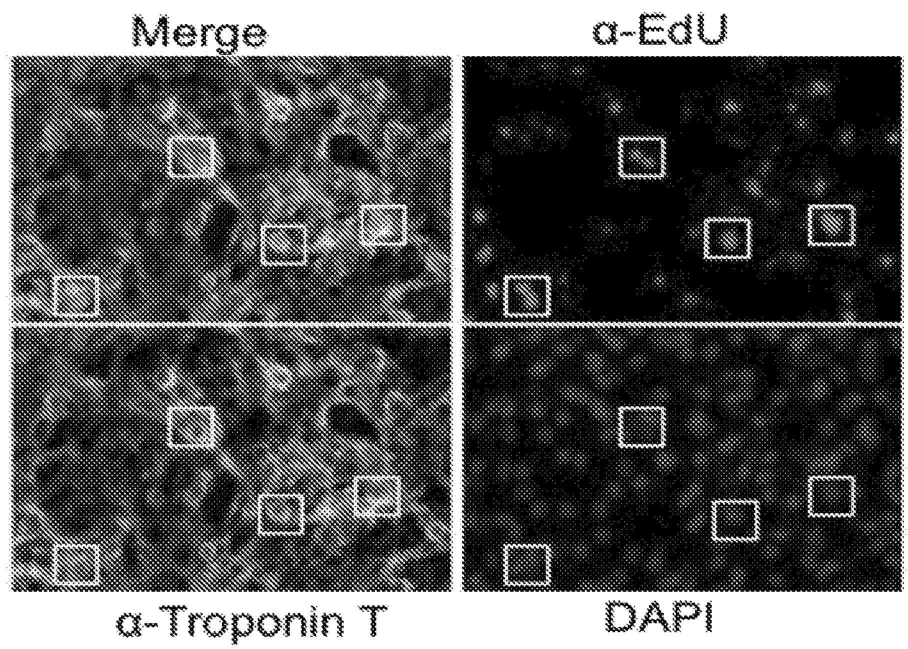
FIG. 7

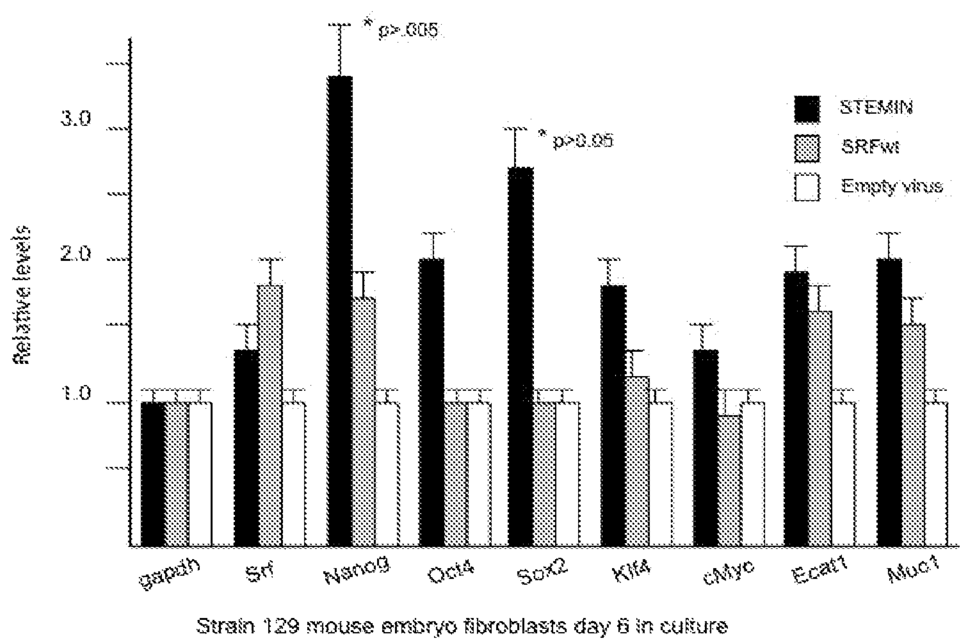
FIG. 8
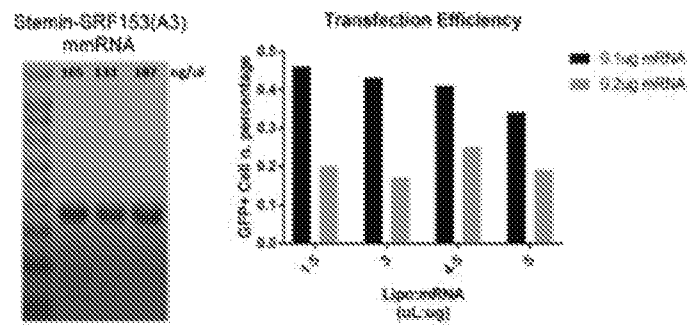
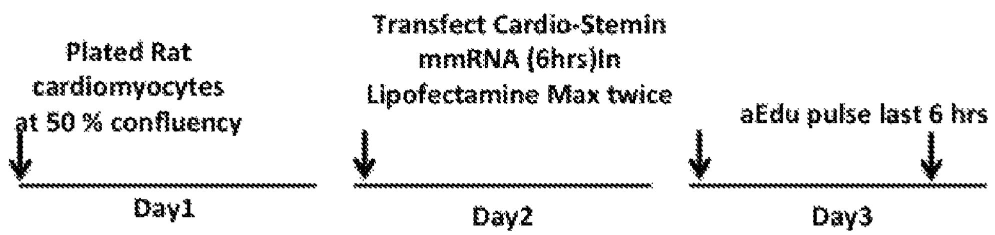
FIGS. 9A-B

EdU/DAPI plotting of TnnT marked Rat cardiac myocytes

* Stands for p<0.05, stands for significance difference

SERUM RESPONSE FACTOR REGENERATES SENESCENT CELLS

PRIORITY

The present application is a national phase application under 35 U.S.C. § 371 of International Application No. PCT/US2018/068203, filed Dec. 31, 2018, which claims benefit of priority to U.S. Provisional Application Ser. No. 62/614,190 filed Jan. 5, 2018, the entire contents of each of which are hereby incorporated by reference.

BACKGROUND

1. Field

The present disclosure relates generally to the fields of cardiology, developmental biology and molecular biology. More particularly, it concerns gene regulation and cellular physiology in cardiomyocytes. Specifically, the invention relates to the use of various transcription factors to reprogram cardiac fibroblasts into cardiomyocytes and the use of such factors in the prevention of scarring and repair in post-myocardial infarction.

2. Description of Related Art

Heart disease is the most serious public health problem facing the United States and the developing world. The loss of cardiomyocytes underlies most causes of heart failure. Normal repair processes are inadequate to deal with extensive myocardial damage. While heart transplantation is the standard for treatment, the limited availability of donor hearts and the risk of rejection restrict its widespread use. Thus, new methods that permit cardiac repair are desperately needed.

Recently, the prospect of repairing damaged myocardium using stem cells has emerged. A variety of different stem cell types from which cardiomyocytes (CMs) could be derived have been proposed including embryonic (ESC), Induced Pluripotent Stem Cells (iPSCs), bone marrow derived mesenchymal stem cells and Cardiac Progenitor Cells (CPCs) from adult cardiac tissue. However, developing therapies with these cell types presents problems. The most common method for obtaining ventricular-like cells from human ESCs allowed CMs to develop for prolonged periods (60 days or greater) in heterogeneous cultures induced by serum or defined protocols. T-tubules in adult ventricular CMs are absent in hES derived CMs and they show poor $Ca^{2+}$ handling properties. T-tubule formation-related genes, CAV3 and BIN1 are absent in both human and murine ES derived CMs resulting in the absence of organized t-tubules, unsynchronized $Ca^{2+}$ transients, impaired contractile properties, and significant arrhythmias in experimental animals. For ESCs, ethical issues, potential for teratoma formation and the need for immunosuppression are obstacles. IPSCs, although they can be autologous, have similar issues with teratoma formation. Thus, improvements in stem cell technologies clearly are necessary to fully exploit this powerful therapeutic approach.

SUMMARY

Thus, in accordance with the present disclosure, there is provided a method of of inducing cell de-differentiation comprising providing to a target cell a STEMIN polypeptide. Providing may comprise delivering a STEMIN polypeptide to said target cell. The STEMIN polypeptide may comprise a heterologous cell permeability peptide (CPP). The target cell may be a cardiomyocyte or may not be a cardiomyocyte, such as a fibroblast, an endothelial cell or a neuronal cell. Providing may comprise delivering a STEMIN expression cassette to said target cell. The expression cassette is comprised in a replicable vector, such as a viral vector, such as an adeno-associated virus (AAV), non-integrated lentivirus, adenoviral vector or retroviral vector. The replicable vector may be a non-viral vector, such as a non-viral vector disposed in a lipid delivery vehicle. Providing may comprise delivering a STEMIN-encoding mRNA, such as a STEMIN-encoding RNA is bound to a nanoparticle, and/or a STEMIN-encoding RNA comprising one or more modified nucleotides, such as 5-methylcytidine-5'-triphosphate and/or pseudouridine-5'-triphosphate.

In another embodiment, there is provided a method of inducing cell de-differentiation in a subject comprising providing to a target cell in said subject a STEMIN polypeptide. Providing may comprise delivering a STEMIN polypeptide to said target cell. The STEMIN polypeptide may comprise a heterologous cell permeability peptide (CPP). The target cell may be a cardiomyocyte or may not be a cardiomyocyte, such as a fibroblast, an endothelial cell or a neuronal cell. Providing may comprise delivering a STEMIN expression cassette to said target cell. The expression cassette is comprised in a replicable vector, such as a viral vector, such as an adeno-associated virus (AAV), non-integrated lentivirus, adenoviral vector or retroviral vector. The replicable vector may be a non-viral vector, such as a non-viral vector disposed in a lipid delivery vehicle. Providing may comprise delivering a STEMIN-encoding mRNA, such as a STEMIN-encoding RNA is bound to a nanoparticle, and/or a STEMIN-encoding RNA comprising one or more modified nucleotides, such as 5-methylcytidine-5'-triphosphate and/or pseudouridine-5'-triphosphate The STEMIN polypeptide, expression construct or mRNA may be delivered 2, 3, 4, 5, 6, 7, 8, 9, 10, 11, 12, 13, 14, 15, 16, 17, 18, 19, 20, 21, 22, 23, 24, 25, 26, 27, 28, 29, or 30 times. The STEMIN polypeptide, expression construct or mRNA may be provided daily. The subject may have suffered a myocardial infarction and said target cell is a cardiomyocyte. The subject may suffer from heart failure and said target cell is a cardiomyocyte. The subject may have suffered non-cardiac tissue damage and said target cell is a fibroblast, an endothelial cell or a neuronal cell. The subject may suffer from heart failure and said target cell is a cardiomyocyte.

In yet another embodiment, there is provided a method preventing or delaying development of cardiac hypertrophy or heart failure in a subject having suffered a myocardial infarct (MI) comprising providing to said subject a STEMIN polypeptide. The method may further comprise administering to said subject a secondary anti-hypertrophic or heart failure therapy. The secondary therapy may be a PKD inhibitor, a beta blocker, an ionotrope, a diuretic, ACE-I, AII antagonist, BNP, a $Ca^{++}$-blocker, or an HDAC inhibitor. Preventing or delaying may comprise preventing or delaying cardiac hypertrophy, or may comprise preventing or delaying one or more of decreased exercise capacity, decreased cardiac ejection volume, increased left ventricular end diastolic pressure, increased pulmonary capillary wedge pressure, decreased cardiac output or cardiac index, increased pulmonary artery pressures, increased left ventricular end systolic and diastolic dimensions, increased left and right ventricular wall stress, increased wall tension, decreased quality of life, and/or increased disease related morbidity or mortality. The STEMIN polypeptide may administered to said subject, or STEMIN expression cassette may be administered to said subject, or STEMIN-encoding mRNA may be administered to said subject. The method may further comprise administering an anti-inflammatory agent to said subject.

Also provided are:

- a method of reducing a decrease in exercise tolerance of a subject having suffered a myocardial infarction comprising providing to said subject a STEMINs polypeptide;
- a method of reducing hospitalization of a subject having suffered a myocardial infarction comprising providing to said subject a STEMINs polypeptide;
- a method of improving quality of life of a subject having suffered a myocardial infarction comprising providing to said subject a STEMINs polypeptide;
- a method of decreasing morbidity of a subject having suffered a myocardial infarction comprising providing to said subject a STEMINs polypeptide; and a method of decreasing mortality of a subject having suffered a myocardial infarction comprising providing to said subject a STEMINs polypeptide.

Also provided is a polypeptide comprising at least 22 residues of the sequence SGAKPGKKTRGRVKIKMEFIDNKLRRYTTFSKRKTGIMKKAYELSTLT (SEQ ID NO: 1) and a mutation or mutations selected from an insertion, deletions or substitution in region of KMEFIDN (SEQ ID NO: 2). The polypeptide may include the complete SRF polypeptide but contains one of said mutations. The polypeptide may be 25, 30, 40, 50, 60 75, 100, 125, 150, 200, 250, 300, 350, 400, 450, 500, 508 or 511 residues in length. The polypeptide may comprise the sequence SGAKPGKKTRGRVKIKMEFIDNKLRRYTTFSKRKTGIMKKAYELSTLT (SEQ ID NO: 1) and a mutation or mutations selected from an insertion, deletions or substitution in region of KMEFIDN (SEQ ID NO: 2). The mutation may be a substitutions of residue 147 and/or 153 of SRF, a deletion of residues 147 and/or 153 of SRF, and a one to three residue insertion adjacent to or within 2-3 residues of residues 147 and/or 153 of SRF. The insertion may be a triple alanine insertion.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 6A-B. Doxycycline induced lentiviral Cardio-Stemin caused rat myocyte DNA synthesis. Top panel shows the Tetracycline responsive cloning vector, Ptet-LTR1 and Dox induced expression of SRF and Cardio-Stemin EdU (green fluorescence) labels newly synthesized DNA.

FIG. 7. Synthetic Cardio-Stemin mmRNA drives adult rat myocyte replication. The boxes show recently replicated cells. Dilute 0.75 μL Lipofectamine in 25 μL serum free DMEM. Mix well and incubate for 10 min. at room temperature. Next prepare diluted mmRNA master mix by adding 0.5 μg mmRNA to 25 μL serum free DMEM. Mix well. And then add together for a total volume 50 μl complex added to cells dropwise.

FIG. 8. Viral infections of STEMIN in mouse embryo fibroblasts.

FIGS. 9A-B. Transfection protocol for Stemin synthetic mmRNA into rat cardiac myocytes. FIG. 9A shows polyacrylamide electrophoresis of 3 samples of Stemin-SRF153 (A) mutant synthetic RNA. Adjacent panel shows transfection efficiency with a GFP synthetic RNA and Lipofectamine FIG. 9B shows the transfection protocol of rat myocytes with Stemin mmRNA. Panel C shows the assay conditions for staining for troponinT2, alpha Edu incorporation into synthesized DNA and DAPI staining to provide a count for nuclei.

DETAILED DESCRIPTION OF ILLUSTRATIVE EMBODIMENTS

Figures 1, 2:
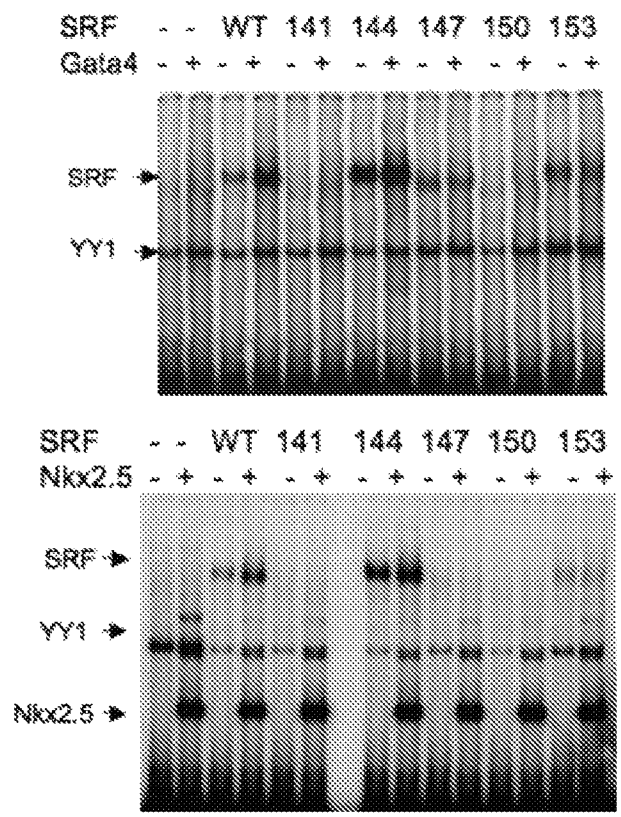
FIG. 1. The inventors used site-directed PCR mutagenesis to create amino acid mutations at specified residues across the SRF core domain. Residues were changed to alanines (giving a neutral charge and removing potential interacting side chains. SEQ ID NOS: 53-58, top to bottom.
FIG. 2. Srf null mouse embryonic stem cells cell were infected with Lenti-virus expressing wild-type SRF and SRF triple alanine mutants. Co-infectants of cardiac actin promoter-luciferase reporter, Gata4 and or Nkx2.5 and SRF mutants FIG. 3. Virtually every SRF mutant caused an increase in the expression of stem cell marker genes Nanog and Oct4 gene expression in the SRF null mouse embryonic stem cells and the strongest induction was elicited by the lentiviral infections with mutants SRF147(A3) and SRF-153(A3).
Figure 3:
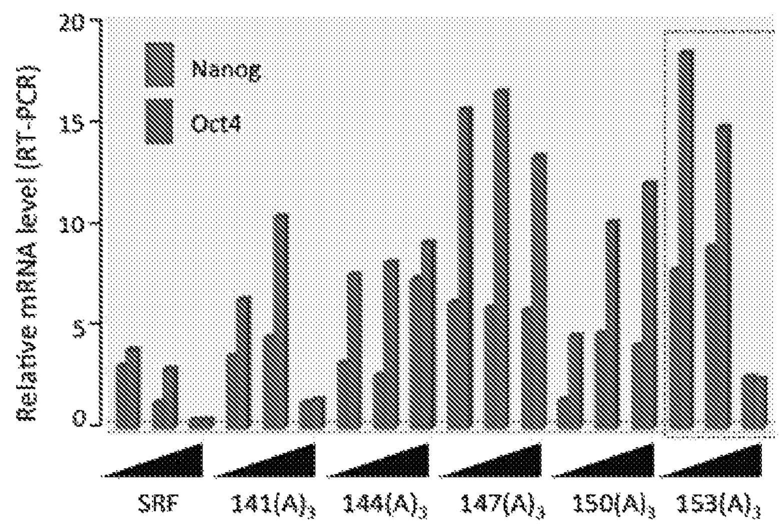

Heart failure is one of the leading causes of morbidity and mortality in the world. In the U.S. alone, estimates indicate that 3 million people are currently living with cardiomyopathy and another 400,000 are diagnosed on a yearly basis. Heart disease and its manifestations, including coronary artery disease, myocardial infarction, congestive heart failure and cardiac hypertrophy, clearly presents a major health risk in the United States today. The cost to diagnose, treat and support patients suffering from these diseases is well into the billions of dollars.

One particularly severe manifestation of heart disease is myocardial infarction (MI). Typically, MI results from an acute thrombocytin coronary occlusion that occurs in a coronary artery as a result of atherosclerosis and causes myocardial cell death, i.e., an infarct. Because cardiomyocytes, the heart muscle cells, are terminally differentiated and generally incapable of cell division, they are generally replaced by scar tissue when they die during the course of an acute myocardial infarction. Scar tissue is not contractile, fails to contribute to cardiac function, and often plays a detrimental role in heart function by expanding during cardiac contraction, or by increasing the size and effective radius of the ventricle, for example, becoming hypertrophic. Cardiac hypertrophy is an adaptive response of the heart to virtually all forms of cardiac disease, including myocardial infarction. While the hypertrophic response is initially a compensatory mechanism that augments cardiac output, sustained hypertrophy can lead to DCM, heart failure, and sudden death. In the United States, approximately half a million individuals are diagnosed with heart failure each year, with a mortality rate approaching 50%.

Treatment with pharmacological agents still represents the primary mechanism for reducing or eliminating the manifestations of heart failure, including those resulting from MIs. Diuretics constitute the first line of treatment for mild-to-moderate heart failure. Unfortunately, many of the commonly used diuretics (e.g., the thiazides) have numerous adverse effects. For example, certain diuretics may increase serum cholesterol and triglycerides. Moreover, diuretics are generally ineffective for patients suffering from severe heart failure. If diuretics are ineffective, vasodilatory agents may be used; the angiotensin converting (ACE) inhibitors (e.g., enalopril and lisinopril) not only provide symptomatic relief, they also have been reported to decrease mortality (Young et al., 1989). Again, however, the ACE inhibitors are associated with adverse effects that result in their being contraindicated in patients with certain disease states (e.g., renal artery stenosis). Similarly, inotropic agent therapy (i.e., a drug that improves cardiac output by increasing the force of myocardial muscle contraction) is associated with a panoply of adverse reactions, including gastrointestinal problems and central nervous system dysfunction.

Recently, the prospect of repairing damaged myocardium using stem cells has emerged. A variety of different stem cell types from which cardiomyocytes (CMs) could be derived have been proposed including embryonic (ESC) (Murry et al., 2006), Induced Pluripotent Stem Cells (iPSCs) (Laflamme et al., 2007), bone marrow derived mesenchymal stem cells (Zhang et al., 2009) and Cardiac Progenitor Cells (CPCs) from adult cardiac tissue (Hare et al., 2012). However, developing therapies with these cell types presents problems. The most common method for obtaining ventricular-like cells from human ESCs allowed CMs to develop for prolonged periods (60 days or greater) in heterogeneous cultures induced by serum or defined protocols (Beltrami et al., 2003; Chong et al., 2014; Kaltman et al., 2011; Baharvand et al., 2006). T-tubules in adult ventricular CMs are absent in hES derived CMs (Baharvand et al., 2006) and they show poor $Ca^{2+}$ handling properties. T-tubule formation-related genes, CAV3 and BIN1 are absent in both human and murine ES derived CMs (Lieu et al., 2009; Marban and Malliaras, 2012; Mercola et al., 2011) resulting in the absence of organized t-tubules, unsynchronized $Ca^{2+}$ transients, impaired contractile properties, and significant arrhythmias in experimental animals. For ESCs, ethical issues, potential for teratoma formation and the need for immunosuppression are obstacles. IPSCs, although they can be autologous, have similar issues with teratoma formation.

The heart is the first functional organ that develops during the embryogenesis of vertebrates and is absolutely dependent on Serum Response Factor (SRF) to generate sarcomeres and the first heart beat. The inventors were the first to show that SRF activity controls sarcomerogenesis in mouse embryos (Niu et al., 2011). The ability for SRF to be the universal "myogenic driver" was totally abrogated in conditional Nkx2.5Cre induced Srf-null embryos and supported the concept that SRF resides at the highest point in the regulatory hierarchy governing sarcomerogenesis (Niu et al., 2011). During mouse heart development, sarcomeric proteins are sequentially assembled into a complex contractile apparatus, with the sarcomere being its most basic unit, to generate the force needed for contraction (Murry et al., 2006; LaFlamme et al., 2007). Fetal cardiomyocytes proliferate accompanied by two consecutive steps. First, sarcomeres must be disassembled to enable chromosome segregation to complete the cell division cycle (Zhang et al., 2009; Hare et al., 2012; Beltrami et al., 2003; Chong et al., 2014). The sarcomere occupies a large volume of the mature cardiomyocyte, which physically impedes mitosis and cytokinesis. Thus, sarcomere disassembly is a prerequisite task for cardiomyocyte proliferation Chong et al., 2014. Next, once disassembly is achieved myocyte replication will proceed. Sarcomeres reassemble from myofibrillar proteins after cell division and contraction resumes Hare et al., 2012). Postnatal cardiomyocyte cell division slows down in new born mice after a week and responds to physiological or pathological challenges after birth through cardiac hypertrophy (Beltrami et al., 2003).

The inventors reasoned that to rejuvenate senescent adult myocytes and expand their number after a cardiac infarct, they need to take myocytes backwards to a more primitive state. They made a discovery that scanning triplet alanine mutations of the N-terminus of SRF's MADS box blocked cardiac differentiation (Niu et al., 2011). One of these mutants, SRF(153A3) named Cardio-Stemin, powerfully activated over 15 stem cell marker genes, in rescue of SRF null murine embryonic stem cells. Cardio-Stemin also inhibited the induction of many cardiac specified genes in virally-infected wild-type ES cells undergoing embryoid formation and cardiac myocyte differentiation. The SRF mutant, Cardio-Stemin is able to affect several steps that drive myocytes back to an earlier proliferative, embryonic-like state and upon withdrawal of Cardio-Stemin, revert to functional myocytes. The same approach can also be applied to non-cardiac cells, such as fibroblasts, and can thus address a variety of other tissue and organ regeneration needs. These and other aspects of the disclosure are described in detail below.

I. SRF AND STEMIN

A. Serum Response Factor

Serum response factor, also known as SRF, is a 67 kd DNA-binding protein that acts as transcription factor. Serum response factor is a member of the MADS (MCM1, Agamous, Deficiens, and SRF) box superfamily of transcription factors (Treisman, 1995). MADS stands for the MCM1, Agamous, Deficiens, and SRF family of transcription factors, which share homology in a MADS-box that mediates homodimerization and DNA binding to a dyad symmetrical A+T-rich DNA consensus sequence (Treisman, 1995). This protein binds to the serum response element (SRE) in the promoter region of target genes. This protein regulates the activity of many immediate early genes, for example c-fos, and thereby participates in cell cycle regulation, apoptosis, cell growth, and cell differentiation. This gene is the downstream target of many pathways; for example, the mitogen-activated protein kinase pathway (MAPK) that acts through the ternary complex factors (TCFs)

SRF is important during the development of the embryo, as it has been linked to the formation of mesoderm. In the fully developed mammal, SRF is crucial for the growth of skeletal muscle. Interaction of SRF with other proteins, such as steroid hormone receptors, may contribute to regulation of muscle growth by steroids. Interaction of SRF with other proteins such as myocardin or Elk-1 may enhance or suppress expression of genes important for growth of vascular smooth muscle. Lack of skin SRF is associated with psoriasis and other skin diseases.

SRF, a 67 kd DNA-binding protein, was first discovered by Richard Treisman (Treisman, 1990; 1994; 1995) as a factor that bound to the serum response element in the c-fos promoter. It is the founding member of an ancient DNA binding protein family that shares a highly conserved DNA-binding and dimerization domain termed the MADS box (Li et al., 1996; FIG. 2). There are numerous MADS-box proteins in plants (Treisman 1995), but SRF and the four members of the myocyte enhancer factor-2 (MEF2) family are the only MADS-box proteins found in metazoans (Treisman, 1990). The crystal structures of SRF and MEF2 have revealed commonalities in their modes of DNA binding, which are reflected in the similar sequences of their binding sites (Shore and Sharrocks, 1995). SRF target genes are characterized by the presence of single or multiple copies of the SRF binding consensus element CC(A/T)2A(A/T)3GG, otherwise known as the CArG box. CArG boxes are found primarily in genes involved with contractility, cell movement, and cell growth signaling. The full spectrum of functional CArG elements in the genome was recently named the CArGome (Boxer et al., 1989) representing known and novel SRF-binding sequences with preferred base composition across the CArG element. A central problem in development is to understand how SRF activity can be differentially controlled according to cell type and or signaling pathway. In fibroblasts, SRF controls transcription of many cellular 'immediate-early' genes, whose expression is activated by growth factor or mitogenic stimuli (McDonald et al., 2006) such as c-fos and Egr-1, important targets for the ERK signaling pathways that converge on SRF has a core domain of 90 amino acids required for dimerization and sequence specific DNA binding (Sharrocks, 1995; Treisman, 1995). The highly conserved MADS box within this core domain is necessary for critical interactions with co-accessory factors (Pellegrini, 1995). Furthermore, all DNA contacts occur within the N-terminal portion of the MADS box, and SRF-SRF dimerization is mediated by elements within the MADS box together with additional residues from the immediately adjacent C terminal region (Pellegrini, 1995). Hence a comprehensive dissection of the SRF core domain and especially of the MADS box is essential for understanding how SRF regulates cardiomyogenesis.

The full length SRF sequence is shown below:

```
                                                   (SEQ ID NO: 3)
1         10         20         30         40         50
MLPTQAGAAA ALGRGSALGG SLNRTPTGRP GGGGGTRGAN GGRVPGNGAG

        60         70         80         90        100
LGPGRLEREA AAAAATTPAP TAGALYSGSE GDSESGEEEE LGAERRGLKR

       110        120        130        140        150
SLSEMEIGMV VGGPEASAAA TGGYGPVSGA VSGAKPGKKT RGRVKIKMEF

       160        170        180        190        200
IDNKLRRYTT FSKRKTGIMK KAYELSTLTG TQVLLLVASE TGHVYTFATR

       210        220        230        240        250
KLQPMITSET GKALIQTCLN SPDSPPRSDP TTDQRMSATG FEETDLTYQV

       260        270        280        290        300
SESDSSGETK DTLKPAFTVT NLPGTTSTIQ TAPSTSTTMQ VSSGPSFPIT

       310        320        330        340        350
NYLAPVSASV SPSAVSSANG TVLKSTGSGP VSSGGLMQLP TSFTLMPGGA

       360        370        380        390        400
VAQQVPVQAI QVHQAPQQAS PSRDSSTDLT QTSSSGTVTL PATIMTSSVP

       410        420        430        440        450
TTVGGHMMYP SPHAVMYAPT SGLGDGSLTV LNAFSQAPST MQVSHSQVQE

       460        470        480        490        500
PGGVPQVFLT ASSGTVQIPV SAVQLHQMAV IGQQAGSSSN LTELQVVNLD

       508
TAHSTKSE
```

The SRF core domain sequence (aa 132-223) is shown below (MADS box in bold):

```
                                              (SEQ ID NO: 4)
132SGAKPGKKTRGRVKIKMEFIDNKLRRYTTFSKRKTGIMKKAYELSTLT179
  N-terminal extension          αI coil

180GTQVLLLVA SETGHVYTFATRKLQPMITS ETGKALIQTCLNSPD223
   βi coil β-loop βII coil       αII coil
```

There are likely to be distinct sites for interactions with cofactors that regulate transcription of proliferation genes and others for interactions with cofactors that regulate transcription of differentiation genes. One key site that modulates SRF's transcriptional activity towards proliferation genes is well-known—a region in the βII coil of the MADS box (aa 194-198) that binds to the Ets protein Elk1 to form a ternary complex with SRF and the c-fos promoter, leading to increased transcription of that proliferative gene (Ling, 1998). Much less is known about sites where cofactors converge on ternary complex factors (TCF). SRF is able to recruit accessory factors that comprise TCFs (Dalton and Treisman, 1992, Hill et al., 1993). TCFs include the proteins Elk-1, Sap-1, Net/ERP/Sap-2 and Fli-1 (Shore and Sharrocks, 1994, Dalgleish and Sharrocks, 2000). Even the SRF gene is controlled by itself during cellular growth, leading to a positive autoregulatory loop. Phosphorylation of the Elk-1 B-box enhanced co-association with SRF and stimulated growth factor-driven SRF gene activity (Dalton and Treisman, 1992). SRF and related MADS-box factors are essential for post-replicative cell-type-specific gene regulation, namely neuronal-specific and muscle-specific gene expression (McDonald et al., 2006). The alpha-actin genes have served as paradigms for SRF-directed myocyte-specific gene expression (Chen and Schwartz, 1996; Chen et al., 1996a; Belaguli et al., 2000; Sepulveda et al., 2002). This includes cardiac, skeletal and vascular muscle actin genes. For example, the combinatorial action of SRF, Nkx-2 and GATA-4, as part of a multicomponent transcriptional regulatory complex, was shown to regulate the cardiac alpha-actin gene in early cardiac progenitor cells (Chen and Schwartz; 1996; Chen et al., 1996a; Belaguli et al., 2000; Sepulveda et al., 2002). In myogenic cells, members of the GATA family of zinc finger transcription factors and the Nkx2.5 family of homeodomain proteins (Sepulveda et al., 2002), can form complexes both with SRF and their own adjacent recognition site. Myocardin is another important cofactor which drives smooth muscle gene activity by association with SRF but not directly to DNA (Wang et al., 2001; 2002; Cen et al., 2003; Miralles et al., 2003).

The inventors revealed that SRF's interactions with Nkx2.5 and GATA4 map aa 142-171 in the MADS box. Nkx2.5 and GATA4 markedly increase both SRF binding to the cardiac α-actin promoter and transcription of this differentiation gene (Sepulveda, 2002). Val194, Thr196 are essential for complex formation with Elk-1, myocardin and MAL (Ling, 1998; Wang, 2004; Zaromytidou, 2006). The X-ray crystal structure of the SRF core bound to DNA (Pellegrini, 1995; Mo, 2001) has revealed the following sites to be important for direct nucleotide binding: N-terminal extension (Thr140, Gly142, Arg143, Val144, Lys145 and Ile146); αI helix (Arg156, Thr160, Lys164, Ser 162, Arg 164, Lys165, Lys170 and Lys171). Thr159 and Ser162 are important for DNA bending, DNA binding affinity, transcriptional activation, and cell growth (Mo 2001). Studies by others have revealed the following: a). Lys154 and His193 are needed for both DNA contact and DNA bending (Sharrocks, 1993a; West, 1995); b) Lys154 and Gly142 are important for c-fos SRE binding (Nurrish, 1995). Lys170 and Lys171 are important for co-accessory induced DNA binding (West, 1999). Identifying the sites of interaction with Elk-1, Nkx2.5, GATA4 and myocardin in the region where SRF binds to the SRE is essential to unravel the mechanism of SRF's transcriptional regulation of proliferation or differentiation genes in cardiomyogenesis.

The MADS box is a region for interactions with critical transcription regulating co-accessory factors. There are likely to be distinct sites for interactions with cofactors that regulate transcription of proliferation genes and others for interactions with cofactors that regulate transcription of differentiation genes. One key site that modulates SRF's transcriptional activity towards proliferation genes is well known.—a region in the RI coil of the MADS box (aa 194-198) that binds to the Ets protein Elk1 to form a ternary complex with SRF and the c-fos promoter, leading to increased transcription. Much less is known about sites where cofactors converge to modulate SRF mediated transcription of differentiation genes. Studies from my laboratory revealed that SRF's interactions with Nkx2.5 and GATA4 map approximately between aa142 to aa171 in the MADS box. Nkx2.5 and GATA4 markedly increase both SRF binding to the cardiac α-actin promoter and transcription of this differentiation gene (Belaguli et al., 2000 and Sepulveda et al., 2002). Myocardin and the MRTF's compete for binding at Val194 with Elk-1, but required additional contacts for a productive interaction (Wang et al., 2001; Cen et al., 2003; Wang et al., 2004). Identifying the exact contact sites for Nkx2.5, GATA4, myocardin and MRTF's is essential to unravel the mechanism of their recruitment to SRF in the contexts of different promoters of both proliferative and differentiation genes.

B. Stemin

The inventors generated triplet alanine scanning mutations across the MADS box of SRF to determine if they interfered with the association of these co-accessory factors. SRF's cooperative interactions with Nkx2.5 and GATA4 mapped to the N-extension of the MADS box, was blocked by several SRF triple alanine mutants as shown by inhibition of cardiac actin promoter-luciferase reporter. Surprisingly, virtually every SRF mutant caused an increase in Nanog and Oct4 gene expression and the strongest induction was elicited by mutants SRF1-47(A3) and SRF-153(A3). FIG. 1 shows several Stemin molecules. The applicants therefore contemplate the generation of mutation—insertions (single, double or triple), deletions and substitutions (conservative or non-conservative) of the region of residues 147-153 of SRF.

In generally, a Stemin molecule is any polypeptide including all or at least 22 residues of the sequence 132-SGAKPGKKTRGRVKIKMEFIDNKLRRYTTFSKRKTGIMKKAYELSTLT-179 (SEQ ID NO: 1) that binds up transcription factors Nkx2.5 and/or GATA4 but that causes a block in differentiation, thereby allowing cell replication to occur.

More specifically, a Stemin molecule will contain a mutation or mutations that block Nkx2.5 and/or GATA4 interactions within the residues 132 and 179 (N-terminus through the alpha 1 domain 179 aa of the MADS box) or SRF. Additional mutations within this same region may also insert, remove or change one or more residues that stimulate stem cell factor induction such as Nanog and Oct4. More specifically, the mutations may be substitutions of residues 147 and/or 153, deletions of residues 147 and/or 153, and one to three residue insertions adjacent to or within 2-3 residues of residues 147 and/or 153.

Particular Stemin molecules are shown below:

(SEQ ID NO: 5)

1 10 20 30 40 50
MLPTQAGAAA ALGRGSALGG SLNRTPTGRP GGGGGTRGAN GGRVPGNGAG 60 70 80 90 100
LGPGRLEREA AAAAATTPAP TAGALYSGSE GDSESGEEEE LGAERRGLKR 110 120 130 140 150
SLSEMEIGMV VGGPEASAAA TGGYGPVSGA VSGAKPGKKT RGRVKIKMEF 160 170 180 190 200
IDAAARRYTT FSKRKTGIMK KAYELSTLTG TQVLLLVASE TGHVYTFATR 210 220 230 240 250
KLQPMITSET GKALIQTCLN SPDSPPRSDP TTDQRMSATG FEETDLTYQV 260 270 280 290 300
SESDSSGETK DTLKPAFTVT NLPGTTSTIQ TAPSTSTTMQ VSSGPSFPIT 310 320 330 340 350
NYLAPVSASV SPSAVSSANG TVLKSTGSGP VSSGGLMQLP TSFTLMPGGA 360 370 380 390 400
VAQQVPVQAI QVHQAPQQAS PSRDSSTDLT QTSSSGTVTL PATIMTSSVP 410 420 430 440 450
TTVGGHMMYP SPHAVMYAPT SGLGDGSLTV LNAFSQAPST MQVSHSQVQE 460 470 480 490 500
PGGVPQVFLT ASSGTVQIPV SAVQLHQMAV IGQQAGSSSN LTELQVVNLD

508
TAHSTKSE (SEQ ID NO: 6)

1 10 20 30 40 50
MLPTQAGAAA ALGRGSALGG SLNRTPTGRP GGGGGTRGAN GGRVPGNGAG 60 70 80 90 100
LGPGRLEREA AAAAATTPAP TAGALYSGSE GDSESGEEEE LGAERRGLKR 110 120 130 140 150
SLSEMEIGMV VGGPEASAAA TGGYGPVSGA VSGAKPGKKT RGRVKIAAAF 160 170 180 190 200
IDNKLRRYTT FSKRKTGIMK KAYELSTLTG TQVLLLVASE TGHVYTFATR 210 220 230 240 250
KLQPMITSET GKALIQTCLN SPDSPPRSDP TTDQRMSATG FEETDLTYQV 260 270 280 290 300
SESDSSGETK DTLKPAFTVT NLPGTTSTIQ TAPSTSTTMQ VSSGPSFPIT 310 320 330 340 350
NYLAPVSASV SPSAVSSANG TVLKSTGSGP VSSGGLMQLP TSFTLMPGGA 360 370 380 390 400
VAQQVPVQAI QVHQAPQQAS PSRDSSTDLT QTSSSGTVTL PATIMTSSVP 410 420 430 440 450
TTVGGHMMYP SPHAVMYAPT SGLGDGSLTV LNAFSQAPST MQVSHSQVQE 460 470 480 490 500
PGGVPQVFLT ASSGTVQIPV SAVQLHQMAV IGQQAGSSSN LTELQVVNLD

508
TAHSTKSE

III. PROTEIN THERAPY

The present disclosure, in one aspect, relates to the production and formulation of STEMINs as well as their delivery to cells, tissues or subjects. In general, recombinant production of proteins is well known and is therefore no described in detail here. The discussion of nucleic acids and expression vectors, found below, is however incorporated in this discussion.

A. Purification of Proteins

It will be desirable to purify proteins according to the present disclosure. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present disclosure concern the purification, and in particular embodiments, the substantial purification, of an encoded protein or peptide. The term "purified protein" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein composition that has been subjected to fractionation to remove various other components, and which composition substantially retains its expressed biological activity. Where the term "substantially purified" is used, this designation will refer to a composition in which the protein forms the major component of the composition, such as constituting about 50%, about 60%, about 70%, about 80%, about 90%, about 95% or more of the proteins in the composition.

Various methods for quantifying the degree of purification of the protein will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Concanavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present disclosure is discussed below.

B. Cell Permeability Peptides

The present disclosure contemplates the use of a cell permeability peptide (also called a cell delivery peptide, or cell transduction domain) linked to transcription factors. Such domains have been described in the art and are generally characterized as short amphipathic or cationic peptides and peptide derivatives, often containing multiple lysine and arginine resides (Fischer, 2007). Other examples are shown in Table 1, below.

TABLE 1

CDD/CTD PEPTIDES

| | SEQ ID NO: | | SEQ ID NO: |
|---|---|---|---|
| GALFLGWLGAAGSTMGAKKKRKV | 9 | QAATATRGRSAASRPTERPRAPARSASRPRRPVE | 31 |
| RQIKIWFQNRRMKWKK | 10 | MGLGLHLLVLAAALQGAKSKRKV | 32 |
| RRMKWKK | 11 | AAVALLPAVLLALLAPAAANYKKPKL | 33 |
| RRWRRWWRRWWRRWRR | 12 | MANLGYWLLALFVTMWTDVGLCKKRPKP | 34 |
| RGGRLSYSRRRFSTSTGR | 13 | LGTYTQDFNKFHTFPQTAIGVGAP | 35 |
| YGRKKRRQRRR | 14 | DPKGDPKGVTVTVTVTVTGKGDPXPD | 36 |
| RKKRRQRRR | 15 | PPPPPPPPPPPPP | 37 |
| YARAAARQARA | 16 | VRLPPPVRLPPPVRLPPP | 38 |
| RRRRRRRR | 17 | PRPLPPPRPG | 39 |
| KKKKKKKK | 18 | SVRRRPRPPYLPRPRPPPFFPPRLPPRIPP | 40 |
| GWTLNSAGYLLGKINLKALAALAKXIL | 19 | TRSSRAGLQFPVGRVHRLLRK | 41 |
| LLILLRRRIRKQANAHSK | 20 | GIGKFLHSAKKFGKAFVGEIMNS | 42 |
| SRRHHCRSKAKRSRHH | 21 | KWKLFKKIEKVGQNIRDGIIKAGPAVAVVGQATQIAK | 43 |
| NRARRNRRRVR | 22 | ALWMTLLKKVLKAAAKAALNAVLVGANA | 44 |
| RQLRIAGRRLRGRSR | 23 | GIGAVLKVLTTGLPALISWIKRKRQQ | 45 |
| KLIKGRTPIKFGK | 24 | INLKALAALAKKIL | 46 |
| RRIPNRRPRR | 25 | GFFALIPKIISSPLPKTLLSAVGSALGGSGGQE | 47 |
| KLALKLALKALKAALKLA | 26 | LAKWALKQGFAKLKS | 48 |
| KLAKLAKKLAKLAK | 27 | SMAQDIISTIGDLVKWIIQTVNXFTKK | 49 |

TABLE 1-continued

| CDD/CTD PEPTIDES | SEQ ID NO: | | SEQ ID NO: |
|---|---|---|---|
| GALFLGFLGAAGSTNGAWSQPKK KRKV | 28 | LLGDFFRKSKEKIGKEFKRIVQRIKQ RIKDFLANLVPRTES | 50 |
| KETWWETWWTEWSQPKKKRKV | 29 | PAWRKAFRWAWRMLKKAA | 51 |
| LKKLLKKLLKKLLKKLLKKL | 30 | KLKLKLKLKLKLKLKLKL | 52 |

C. Delivery of Polypeptides

In general, proteins are delivered to cells as a formulation that promotes entry of the proteins into a cell of interest. In a most basic form, lipid vehicles such as liposomes. For example, liposomes, which are artificially prepared vesicles made of lipid bilayers have been used to delivery a variety of drugs. Liposomes can be composed of naturally-derived phospholipids with mixed lipid chains (like egg phosphatidylethanolamine) or other surfactants. In particular, liposomes containing cationic or neutral lipids have been used in the formulation of drugs. Liposomes should not be confused with micelles and reverse micelles composed of monolayers, which also can be used for delivery.

A wide variety of commercial formulations for protein delivery are well known including PULSin™, Lipodin-Pro, Carry-MaxR, Pro-DeliverIN, PromoFectin, Pro-Ject, Chariot™ Protein Delivery reagent, BioPORTER™, and others.

Nanoparticles are generally considered to be particulate substances having a diameter of 100 nm or less. In contrast to liposomes, which are hollow, nanoparticles tend to be solid. Thus, the drug will be less entrapped and more either embedded in or coated on the nanoparticle. Nanoparticles can be made of metals including oxides, silica, polymers such as polymethyl methacrylate, and ceramics. Similarly, nanoshells are somewhat larger and encase the delivered substances with these same materials. Either nanoparticles or nanoshells permit sustained or controlled release of the peptide or mimetic, and can stabilize it to the effects of in vivo environment.

IV. NUCLEIC ACID DELIVERY

As discussed above, in certain embodiments, mRNAs or DNA expression cassettes/constructs/vectors are employed to express STEMINs, either for subsequent purification and delivery to a cell/subject, or for use directly in a genetic-based delivery approach. Expression requires that appropriate signals be provided in the vectors, and include various regulatory elements such as enhancers/promoters from both viral and mammalian sources that drive expression of the genes of interest in cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

A. Regulatory Elements

Throughout this application, the term "expression cassette" is meant to include any type of genetic construct containing a nucleic acid coding for a gene product in which part or all of the nucleic acid encoding sequence is capable of being transcribed and translated, i.e., is under the control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene. An "expression vector" is meant to include expression cassettes comprised in a genetic construct that is capable of replication, and thus including one or more of origins of replication, transcription termination signals, poly-A regions, selectable markers, and multipurpose cloning sites.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In certain embodiments, viral promotes such as the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized. Further, selection of a promoter that is regulated in response to specific physiologic signals can permit inducible expression of the gene product.

Enhancers are genetic elements that increase transcription from a promoter located at a distant position on the same molecule of DNA Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters/enhancers and inducible promoters/enhancers that could be used in combination with the nucleic acid encoding a gene of interest in an expression construct (Table 2 and Table 3). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

| Promoter and/or Enhancer | |
|---|---|
| Promoter/Enhancer | References |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984: Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988: Horlick et al., 1989; Johnson et al. 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981: Tyndell et al., 1981; Dandolo et al., 1983; de Villiers et al., 1984; Hen et al., 1986; Satake et al., 1988: Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |

TABLE 2-continued

| Promoter and/or Enhancer | |
|---|---|
| Promoter/Enhancer | References |
| Papilloma Virus | Campo et al., 1983; Lusky et al., 1983; Spandidos and/or Wilkie, 1983: Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

| Inducible Elements | | |
|---|---|---|
| Element | Inducer | References |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | ElA | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | ElA, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Of particular interest are fibroblast specific promoters, such as Fibroblast-Specific Protein 1 (FSP1) promoter (Okada et al., 1998); collagen 1A1 (COL1A1) promoter (Hitraya et al., 1998) and Periostin (Postn) promoter (Joseph et al., 2008). Other promoters include muscle specific promoters and cardiac specific promoters such as the myosin light chain-2 promoter (Franz et al., 1994; Kelly et al., 1995), the α-actin promoter (Moss et al., 1996), the troponin 1 promoter (Bhaysar et al., 1996); the $Na^+/Ca^{2+}$ exchanger promoter (Barnes et al., 1997), the dystrophin promoter (Kimura et al., 1997), the α7 integrin promoter (Ziober and Kramer, 1996), the brain natriuretic peptide promoter (LaPointe et al., 1988), the αB-crystallin/small heat shock protein promoter (Gopal-Srivastava, 1995), α-myosin heavy chain promoter (Yamauchi-Takihara et al., 1989) and the ANF promoter (LaPointe et al., 1988).

Where a cDNA insert is employed, one will typically desire to include a polyadenylation signal to effect proper polyadenylation of the gene transcript. The nature of the polyadenylation signal is not believed to be crucial to the successful practice of the disclosure, and any such sequence may be employed such as human growth hormone and SV40 polyadenylation signals. Also contemplated as an element of the expression cassette is a terminator. These elements can serve to enhance message levels and to minimize read through from the cassette into other sequences.

B. Multigene Constructs and IRES

In certain embodiments of the disclosure, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

C. Delivery of mRNAs and Expression Vectors

There are a number of ways in which mRNAs and expression vectors may introduced into cells. In certain embodiments of the disclosure, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

One of the preferred methods for in vivo delivery involves the use of an adeno-associated virus (AAV) expression vector. AAV can infect non-dividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

Another expression vector may comprise a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

There are certain limitations to the use of retrovirus vectors in all aspects of the present disclosure. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. The lentiviral genome and the proviral DNA have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTRs serve to promote transcription and polyadenylation of the virion RNA's. The LTR contains all other cis-acting sequences necessary for viral replication. Lentiviruses have additional genes including vif, vpr, tat, rev, vpu, nef and vpx.

Lentiviral vectors are known in the art, see Naldini et al., (1996); Zufferey et al., (1997); U.S. Pat. Nos. 6,013,516; and 5,994,136. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest.

Other viral vectors may be employed as expression constructs in the present disclosure. Vectors derived from viruses such as vaccinia virus (Ridgeway, 1988; Baichwal and Sugden, 1986; Coupar et al., 1988) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of mRNAs and expression constructs into cultured mammalian cells also are contemplated by the present disclosure. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), RNA- or DNA-loaded liposomes (Nicolau and Sene, 1982; Fraley et al., 1979), lipofectamine-RNA or -DNA complexes, cell sonication (Fechheimer et al., 1987), gene bombardment using high velocity microprojectiles (Yang et al., 1990), receptor-mediated transfection (Wu and Wu, 1987; Wu and Wu, 1988), and nanoparticle delivery. Some of these techniques may be successfully adapted for in vivo or ex vivo use.

The term "nanoparticle" is an object that has a diameter between about 2 nm to about 200 nm (e.g., between 10 nm and 200 nm, between 2 nm and 100 nm, between 2 nm and 40 nm, between 2 nm and 30 nm, between 2 nm and 20 nm, between 2 nm and 15 nm, between 100 nm and 200 nm, and between 150 nm and 200 nm). Non-limiting examples of nanoparticles include the therapeutic nanoparticles described herein. Therapeutic nanoparticles described herein can contain a core of a magnetic material (e.g., a therapeutic magnetic nanoparticle). In some embodiments, the magnetic material or particle can contain a diamagnetic, paramagnetic, superparamagnetic, or ferromagnetic material that is responsive to a magnetic field. Non-limiting examples of therapeutic magnetic nanoparticles contain a core of a magnetic material containing a metal oxide selected from the group of: magnetite; ferrites (e.g., ferrites of manganese, cobalt, and nickel); Fe(II) oxides, and hematite, and metal alloys thereof. The core of magnetic material can be formed by converting metal salts to metal oxides using methods known in the art (e.g., Kieslich et al., Inorg. Chem. 2011). In some embodiments, the nanoparticles contain cyclodextrin gold or quantum dots. Non-limiting examples of methods that can be used to generate therapeutic magnetic nanoparticles are described in Medarova et al., Methods Mol. Biol. 555:1-13, 2009; and Medarova et al., Nature Protocols 1:429-431, 2006. Additional magnetic materials and methods of making magnetic materials are known in the art. In some embodiments of the methods described herein, the position or localization of therapeutic magnetic nanoparticles can be imaged in a subject (e.g., imaged in a subject following the administration of one or more doses of a therapeutic magnetic nanoparticle).

In some embodiments, the therapeutic nanoparticles do not contain a magnetic material. In some embodiments, a therapeutic nanoparticle can contain, in part, a core of containing a polymer (e.g., poly(lactic-co-glycolic acid)). Skilled practitioners will appreciate that any number of art known materials can be used to prepare nanoparticles, including, but are not limited to, gums (e.g., Acacia, Guar), chitosan, gelatin, sodium alginate, and albumin. Additional polymers that can be used to generate the therapeutic nanoparticles described herein are known in the art. For example, polymers that can be used to generate the therapeutic nanoparticles include, but are not limited to, cellulosics, poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolides) (PLGA), poly anhydrides, polyorthoesters, polycyanoacrylate and polycaprolactone.

Skilled practitioners will appreciate that the material used in the composition of the nanoparticles, the methods for preparing, coating, and methods for controlling the size of the nanoparticles can vary substantially. However, these methods are well known to those in the art. Key issues include the biodegradability, toxicity profile, and pharmacokinetics/pharmacodynamics of the nanoparticles. The composition and/or size of the nanoparticles are key determinants of their biological fate. For example, larger nanoparticles are typically taken up and degraded by the liver, whereas smaller nanoparticles (<30 nm in diameter) typically circulate for a long time (sometimes over 24-hr blood half-life in humans) and accumulate in lymph nodes and the interstitium of organs with hyperpermeable vasculature, such as tumors.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the disclosure, the expression construct may simply consist of naked recombinant RNA or DNA. Transfer may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the disclosure for transferring a naked RNA or DNA into cells may involve particle bombardment. This method depends on the ability to accelerate DNA-coated microprojectiles to a high velocity allowing them to pierce cell membranes and enter cells without killing them (Klein et al., 1987).

Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads. Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present disclosure.

In a further embodiment of the disclosure, the mRNA or expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection. A reagent known as Lipofectamine2000™ is widely used and commercially available.

In certain embodiments of the disclosure, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present disclosure. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

V. METHODS OF TREATMENT

A. Post Myocardial Infarction and Other Cardiac Ischemic Events

The present disclosure provides for new post-MI therapies and types of other cardiac ischemia. In one embodiment of the present disclosure, methods for the treatment of subjects following an MI provides for one or more of the following outcomes as compared to an untreated patient: increased exercise capacity, increased blood ejection volume, decreased left ventricular end diastolic pressure, decreased pulmonary capillary wedge pressure, increased cardiac output, improved cardiac index, decreased pulmonary artery pressures, decreased left ventricular end systolic and diastolic dimensions, and decreased left ventricular wall stress, decreased wall tension and decreased wall thickness-same for right ventricle. In addition, the treatment may prevent progression to cardiac hypertrophy and ultimately heart failure.

Treatment regimens would vary depending on the clinical situation. However, in general, the treatment would begin at a time following an MI when the patient has been stabilized, but before significant cardiac fibroblast mobilization and scarring has begun. The patient may or may not be undergoing one or more other therapies for either prevention or treatment of an MI, or prevention or treatment of MI-related sequelae. This would mean initiating a treatment within about 24, 36, 48, 72, 96 hours of an MI, or within about 5, 6, 7, 8, 9 or 10 days of an MI. The therapy may continue for as long as cardiac fibroblasts would be active within the ischemic zone, such as up to 7 days, 14 days 21 days, 28 days, 1 month, 2 months, 3 months or longer.

1. Combined Therapies

In another embodiment, it is envisioned to use a STEMIN of the present disclosure in combination with other MI and post-MI therapeutic modalities, such as those discussed above. Combinations may be achieved by contacting cardiac cells/patients with a single composition or pharmacological formulation that includes both agents, or by contacting the cell with two distinct compositions or formulations, at the same time, wherein one composition includes the expression construct and the other includes the agent. Alternatively, the therapy using STEMIN may precede or follow administration of the other agent(s) by intervals ranging from minutes to weeks. In embodiments where the other agent and STEMIN are applied separately to the cardiac cells/patient, one would generally ensure that a significant period of time did not expire between the time of each delivery, such that the agent and STEMIN would still be able to exert an advantageously combined effect on the cell. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either transcription factors, or the other agent will be desired. In this regard, various combinations may be employed. By way of illustration, where the transcription factors are "A" and the other agent is "B," the following permutations based on 3 and 4 total administrations are exemplary:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are likewise contemplated. One particular combination therapy involves anti-inflammatory agents, such as steroids or NSAIDs. Other traditional cardiac therapies are discussed below, and may also be usefully combined with the transcription factors discussed above.

2. Standard MI Therapeutic Intervention

Therapies for acute myocardial infarction are designed to restore perfusion as soon as possible to rescue the infracted myocardium. This is typically done by pharmaceutical intervention or by mechanical means, such as percutaneous coronary intervention (PCI) or coronary artery bypass grafting. Recent studies suggest that these treatments are more effective if the following guidelines are followed: <90 min for PCI and <30 min for lytics. Treatments outside these windows were associated with increased mortality and significantly increased risk of readmission for acute myocardial infarction or heart failure.

i. Drug Therapies

Thrombolytic therapy improves survival rates in patients with acute myocardial infarction if administered in a timely fashion in the appropriate group of patients. If PCI capability is not available within 90 minutes, then choice is to administer thrombolytics within 12 hours of onset of symptoms in patients with ST-segment elevation greater than 0.1 mV in 2 or more contiguous ECG leads, new left bundle-branch block (LBBB), or anterior ST depression consistent with posterior infarction. Tissue plasminogen activator (t-PA) is preferred over streptokinase as achieving a higher rate of coronary artery patency; however, the key lies in speed of the delivery.

Aspirin has been shown to decrease mortality and re-infarction rates after myocardial infarction. Again, delivery should be immediate, which should be chewed if possible. The treatment should continue indefinitely in the absence of obvious contraindication, such as a bleeding tendency or an allergy. Clopidogrel may be used as an alternative in cases of a resistance or allergy to aspirin (dose of 300 mg), but a higher dose of clopidogrel may have added benefit.

Platelet glycoprotein (GP) IIb/IIIa-receptor antagonist is another therapy in patients with continuing ischemia or with other high-risk features and to patients in whom a percutaneous coronary intervention (PCI) is planned. Eptifibatide and tirofiban are approved for this use, and abciximab also can be used for 12-24 hours in patients with unstable angina or NSTEMI in whom a PCI is planned within the next 24 hours.

Heparin and other anticoagulant agents have an established role as adjunct agents in patients receiving t-PA, but not in patients receiving streptokinase. Heparin is also indicated in patients undergoing primary angioplasty. Low molecular-weight heparins (LMWHs) have been shown to be superior to UFHs in patients with unstable angina or NSTEMI. Bivalirudin, a direct thrombin inhibitor, has shown promise in STEMI if combined with high-dose clopidogrel.

Nitrates have no apparent impact on mortality rate in patients with ischemic syndromes, but they are useful in symptomatic relief and preload reduction, so much so that all patients with acute myocardial infarction are given nitrates within the first 48 hours of presentation, unless contraindicated (i.e., in RV infarction). Beta-blockers may reduce the rates of reinfarction and recurrent ischemia, and thus are administered to patients with MIs unless a contraindication is present.

ACE inhibitors reduce mortality rates after myocardial infarction and thus are administered as soon as possible as long as no contraindications are and the patient remains stable. ACE inhibitors have the greatest benefit in patients with ventricular dysfunction. Continue ACE inhibitors indefinitely after myocardial infarction. Angiotensin-receptor blockers may be used as an alternative in patients who develop adverse effects, such as a persistent cough, although initial trials need to be confirmed.

ii. PCI and Other Surgical Intervention

PCI is the treatment of choice in most patients with STEMI, assuming a door to balloon time of less than 90 minutes. PCI provides greater coronary patency (>96% thrombolysis), lower risk of bleeding, and instant knowledge about the extent of the underlying disease. Studies have shown that primary PCI has a mortality benefit over thrombolytic therapy. The choice of primary PCI should be individualized to each patient's presentation and timing. Primary PCI is also the treatment of choice in patients with cardiogenic shock, patients in whom thrombolysis failed, and those with high risk of bleeding or contraindications to thrombolytic therapy.

Emergent or urgent coronary artery graft bypass surgery is indicated in patients in whom angioplasty fails and in patients who develop mechanical complications such as a VSD, LV, or papillary muscle rupture.

3. Pharmacological Therapeutic Agents

Pharmacological therapeutic agents and methods of administration, dosages, etc., are well known to those of skill in the art (see for example, the "Physicians Desk Reference", Klaassen's "The Pharmacological Basis of Therapeutics", "Remington's Pharmaceutical Sciences", and "The Merck Index, Eleventh Edition", incorporated herein by reference in relevant parts), and may be combined with the disclosure in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

In addition to the transcription factors of the present disclosure, it should be noted that any of the following may be used to develop new therapeutic regimens in combination with the transcription factors.

i. Antihyperlipoproteinemics

In certain embodiments, administration of an agent that lowers the concentration of one of more blood lipids and/or lipoproteins, known herein as an "antihyperlipoproteinemic," may be combined with a cardiovascular therapy according to the present disclosure, particularly in treatment of athersclerosis and thickenings or blockages of vascular tissues. In certain aspects, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof.

Aryloxyalkanoic Acid/Fibric Acid Derivatives Non-limiting examples of aryloxyalkanoic/fibric acid derivatives include beclobrate, enzafibrate, binifibrate, ciprofibrate, clinofibrate, clofibrate (atromide-S), clofibrat acid, etofibrate, fenofibrate, gemfibrozil (lobid), nicofibrate, pirifibrate, ronifibrate, simfibrate and theofibrate.

Resins/Bile Acid Sequesterants. Non-limiting examples of resins/bile acid sequesterants include cholestyramine (cholybar, questran), colestipol (colestid) and polidexide.

HMG CoA Reductase Inhibitors. Non-limiting examples of HMG CoA reductase inhibitors include lovastatin (mevacor), pravastatin (pravochol) or simvastatin (zocor).

Nicotinic Acid Derivatives. Non-limiting examples of nicotinic acid derivatives include nicotinate, acepimox, niceritrol, nicoclonate, nicomol and oxiniacic acid.

Thryroid Hormones and Analogs. Non-limiting examples of thyroid hormones and analogs thereof include etoroxate, thyropropic acid and thyroxine.

Miscellaneous Antihyperlipoproteinemics. Non-limiting examples of miscellaneous antihyperlipoproteinemics include acifran, azacosterol, benfluorex, β-benzalbutyramide, carnitine, chondroitin sulfate, clomestrone, detaxtran, dextran sulfate sodium, 5, 8, 11, 14, 17-eicosapentaenoic acid, eritadenine, furazabol, meglutol, melinamide, mytatrienediol, ornithine, γ-oryzanol, pantethine, pentaerythritol tetraacetate, α-phenylbutyramide, pirozadil, probucol (lorelco), β-sitosterol, sultosilic acid-piperazine salt, tiadenol, triparanol and xenbucin.

ii. Antiarteriosclerotics

Non-limiting examples of an antiarteriosclerotic include pyridinol carbamate.

iii. Antithrombotic/Fibrinolytic Agents

In certain embodiments, administration of an agent that aids in the removal or prevention of blood clots may be combined with administration of a modulator, particularly in treatment of athersclerosis and vasculature (e.g., arterial) blockages. Non-limiting examples of antithrombotic and/or fibrinolytic agents include anticoagulants, anticoagulant antagonists, antiplatelet agents, thrombolytic agents, thrombolytic agent antagonists or combinations thereof.

In certain aspects, antithrombotic agents that can be administered orally, such as, for example, aspirin and wafarin (coumadin), are preferred.

Anticoagulants. A non-limiting example of an anticoagulant include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

Antiplatelet Agents. Non-limiting examples of antiplatelet agents include aspirin, a dextran, dipyridamole (persantin), heparin, sulfinpyranone (anturane) and ticlopidine (ticlid).

Thrombolytic Agents. Non-limiting examples of thrombolytic agents include tissue plaminogen activator (activase), plasmin, pro-urokinase, urokinase (abbokinase) streptokinase (streptase), anistreplase/APSAC (eminase).

iv. Blood Coagulants

In certain embodiments wherein a patient is suffering from a hemmorage or an increased likelyhood of hemmoraging, an agent that may enhance blood coagulation may be used. Non-limiting examples of a blood coagulation promoting agent include thrombolytic agent antagonists and anticoagulant antagonists.

Anticoagulant Antagonists. Non-limiting examples of anticoagulant antagonists include protamine and vitamine K1.

Thrombolytic Agent Antagonists and Antithrombotics. Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

v. Antiarrhythmic Agents

Non-limiting examples of antiarrhythmic agents include Class I antiarrythmic agents (sodium channel blockers), Class II antiarrythmic agents (beta-adrenergic blockers), Class II antiarrythmic agents (repolarization prolonging drugs), Class IV antiarrhythmic agents (calcium channel blockers) and miscellaneous antiarrythmic agents.

Sodium Channel Blockers. Non-limiting examples of sodium channel blockers include Class IA, Class IB and Class IC antiarrhythmic agents. Non-limiting examples of Class IA antiarrhythmic agents include disppyramide (norpace), procainamide (pronestyl) and quinidine (quinidex). Non-limiting examples of Class IB antiarrhythmic agents include lidocaine (xylocaine), tocainide (tonocard) and mexiletine (mexitil). Non-limiting examples of Class IC antiarrhythmic agents include encainide (enkaid) and flecainide (tambocor).

Beta Blockers. Non-limiting examples of a beta blocker, otherwise known as a β-adrenergic blocker, a β-adrenergic antagonist or a Class II antiarrhythmic agent, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain aspects, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

Repolarization Prolonging Agents. Non-limiting examples of an agent that prolong repolarization, also known as a Class III antiarrhythmic agent, include amiodarone (cordarone) and sotalol (betapace).

Calcium Channel Blockers/Antagonist. Non-limiting examples of a calcium channel blocker, otherwise known as a Class IV antiarrythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a micellaneous calcium channel blocker such as bencyclane, etafenone, magnesium, mibefradil or perhexiline. In certain embodiments a calcium channel blocker comprises a long-acting dihydropyridine (nifedipine-type) calcium antagonist.

Miscellaneous Antiarrhythmic Agents. Non-limiting examples of miscellaneous antiarrhymic agents include adenosine (adenocard), digoxin (lanoxin), acecainide, ajmaline, amoproxan, aprindine, bretylium tosylate, bunaftine, butobendine, capobenic acid, cifenline, disopyranide, hydroquinidine, indecainide, ipatropium bromide, lidocaine, lorajmine, lorcainide, meobentine, moricizine, pirmenol, prajmaline, propafenone, pyrinoline, quinidine polygalacturonate, quinidine sulfate and viquidil.

vi. Antihypertensive Agents

Non-limiting examples of antihypertensive agents include sympatholytic, alpha/beta blockers, alpha blockers, anti-angiotensin II agents, beta blockers, calcium channel blockers, vasodilators and miscellaneous antihypertensives.

Alpha Blockers. Non-limiting examples of an alpha blocker, also known as an α-adrenergic blocker or an α-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

Alpha/Beta Blockers. In certain embodiments, an antihypertensive agent is both an alpha and beta adrenergic antagonist. Non-limiting examples of an alpha/beta blocker comprise labetalol (normodyne, trandate).

Anti-Angiotension II Agents. Non-limiting examples of anti-angiotension II agents include include angiotensin converting enzyme inhibitors and angiotension II receptor antagonists. Non-limiting examples of angiotension converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-II type-1 receptor blocker (ARBS), include angiocandesartan, eprosartan, irbesartan, losartan and valsartan.

Sympatholytics. Non-limiting examples of a sympatholytic include a centrally acting sympatholytic or a peripherially acting sympatholytic. Non-limiting examples of a centrally acting sympatholytic, also known as a central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin).

Vasodilators. In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexiline, pimefylline, trapidil, tricromyl, trimetazidine, trolnitrate phosphate and visnadine.

In certain aspects, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil Miscellaneous Antihypertensives. Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain aspects, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a suflonamide derivative.

Arylethanolamine Derivatives. Non-limiting examples of arylethanolamine derivatives include amosulalol, bufuralol, dilevalol, labetalol, pronethalol, sotalol and sulfinalol.

Benzothiadiazine Derivatives. Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothiazide, meticrane, metolazone, paraflutizide, polythizide, tetrachlormethiazide and trichlormethiazide.

N-carboxyalkyl(peptide/lactam) Derivatives. Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril.

Dihydropyridine Derivatives. Non-limiting examples of dihydropyridine derivatives include amlodipine, felodipine, isradipine, nicardipine, nifedipine, nilvadipine, nisoldipine and nitrendipine.

Guanidine Derivatives. Non-limiting examples of guanidine derivatives include bethanidine, debrisoquin, guanabenz, guanacline, guanadrel, guanazodine, guanethidine, guanfacine, guanochlor, guanoxabenz and guanoxan.

Hydrazines/Phthalazines. Non-limiting examples of hydrazines/phthalazines include budralazine, cadralazine, dihydralazine, endralazine, hydracarbazine, hydralazine, pheniprazine, pildralazine and todralazine.

Imidazole Derivatives. Non-limiting examples of imidazole derivatives include clonidine, lofexidine, phentolamine, tiamenidine and tolonidine.

Quanternary Ammonium Compounds. Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate.

Reserpine Derivatives. Non-limiting examples of reserpine derivatives include bietaserpine, deserpidine, rescinnamine, reserpine and syrosingopine.

Suflonamide Derivatives. Non-limiting examples of sulfonamide derivatives include ambuside, clopamide, furosemide, indapamide, quinethazone, tripamide and xipamide.

Vasopressors. Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

vii. Treatment Agents for Congestive Heart Failure

Non-limiting examples of agents for the treatment of congestive heart failure include anti-angiotension II agents, afterload-preload reduction treatment, diuretics and inotropic agents.

Afterload-Preload Reduction. In certain embodiments, an animal patient that can not tolerate an angiotension antagonist may be treated with a combination therapy. Such therapy may combine adminstration of hydralazine (apresoline) and isosorbide dinitrate (isordil, sorbitrate).

Diuretics. Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furterene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e g, amiloride, triamterene) or a miscellaneous diuretic such as aminozine, arbutin, chlorazanil, ethacrynic acid, etozolin, hydracarbazine, isosorbide, mannitol, metochalcone, muzolimine, perhexiline, ticrnafen and urea.

Inotropic Agents. Non-limiting examples of a positive inotropic agent, also known as a cardiotonic, include acefylline, an acetyldigitoxin, 2-amino-4-picoline, amrinone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular aspects, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include amrinone (inocor).

Antianginal Agents Antianginal agents may comprise organonitrates, calcium channel blockers, beta blockers and combinations thereof.

Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

4. Surgical Therapeutic Agents

In certain aspects, the secondary therapeutic agent may comprise a surgery of some type, such as PCI. Surgery, and in particular a curative surgery, may be used in conjunction with other therapies, such as the present disclosure and one or more other pharmacologic agents. Such surgical approaches for vascular and cardiovascular diseases and disorders are well known to those of skill in the art, and are described elsewhere in this document.

B. Non-Cardiac Therapeutic Indications

1. Neuronal Cells

In another aspect, the disclosure provides for methods of generating pluripotent or multiopent cells from neuronal cells. Neurons are postmitotic, and once lost because of injury or degeneration, they do not regenerate in most regions of the mammalian central nervous system. In the CNS, neurons represent a quintessential example of a permanently post-mitotic and differentiated cell type. They are mainly born during embryonic and early postnatal stages, except for in few regions of the adult brain. Once generated, neurons become permanently post-mitotic and do not change their identity for the lifespan of the organism. See Wang and Zhang (2017).

There are many types of neurons. Sensory neurons respond to one particular type of stimuli such as touch, sound, or light and all other stimuli affecting the cells of the sensory organs, and converts it into an electrical signal via transduction, which is then sent to the spinal cord or brain. Motor neurons receive signals from the brain and spinal cord to cause everything from muscle contractions and affect glandular outputs. Interneurons connect neurons to other neurons within the same region of the brain or spinal cord in neural networks.

A typical neuron consists of a cell body (soma), dendrites, and an axon. The term neurite is used to describe either a dendrite or an axon, particularly in its undifferentiated stage. Dendrites are thin structures that arise from the cell body, often extending for hundreds of micrometers and branching multiple times, giving rise to a complex "dendritic tree". An axon (also called a nerve fiber when myelinated) is a special cellular extension (process) that arises from the cell body at a site called the axon hillock and travels for a distance, as far as 1 meter in humans or even more in other species. Most neurons receive signals via the dendrites and send out signals down the axon. Numerous axons, also known as nerve fibers, are often bundled into fascicles, and in the peripheral nervous system, bundles of fascicles make up what the inventors refer to as nerves (like strands of wire make up cables). The cell body of a neuron frequently gives rise to multiple dendrites, but never to more than one axon, although the axon may branch hundreds of times before it terminates. At the majority of synapses, signals are sent from the axon of one neuron to a dendrite of another. There are, however, many exceptions to these rules: for example, neurons can lack dendrites, or have no axon, and synapses can connect an axon to another axon or a dendrite to another dendrite.

In most cases, neurons are generated by special types of stem cells during brain development and childhood. Neurons in the adult brain generally do not undergo cell division. Astrocytes are star-shaped glial cells that have also been observed to turn into neurons by virtue of the stem cell characteristic pluripotency. Neurogenesis largely ceases during adulthood in most areas of the brain. However, there is strong evidence for generation of substantial numbers of new neurons in two brain areas, the hippocampus and olfactory bulb.

Various commercial sources of neuronal cells exist for use in accordance with the disclosed methods. Clinical samples may also be obtained from immunologically compatible donors.

2. Vascular Cells

Another embodiment for application of the disclosed methods is in the context of vascular disease, such as in the treatment of abdominal aortic aneurysms with intima. The walls of large abdominal aortic aneurysms usually exhibit few viable intimal or medial cells, and it is thus not possible to induce cell proliferation. A protective mechanism against aneurysm expansion will involve the application of Stemin to vasculature tissue undergoing aneurysms, or any other form of vascular disease where the is degradation, damage or loss of vascular material. Other aneurysms include carotid and cerebellar artery aneurysms.

Analyses of clinical specimens of the aneurysm wall demonstrate some characteristic findings associated with vascular aneurysms, including chronic infiltration of inflammatory cells, degradation of extracellular matrix, and apoptosis of smooth muscle cells (Linder et al., 1991; Hoshina et al., 2004). Because SMCs in the vascular wall are an important source of matrix molecules such as elastin and collagen, enhanced replication of smooth muscle cells of the medial layer will stabilize aortic integrity. Also, vascular endothelial cells are also critical in the generation of new blood vessels, and will replicate in response to Stemin treatment. Stemin delivery to the aortic wall or cerebral vasculature by catheter-based delivery into local or regioal blood vessels will increase smooth muscle cell and endothelial cell proliferation in the vasculature walls and reduce the severity of is associated with aneurysms.

C. Drug Formulations and Routes for Administration to Patients

Where clinical applications are contemplated, pharmaceutical compositions will be prepared in a form appropriate for the intended application. Generally, this will entail preparing compositions that are essentially free of pyrogens, as well as other impurities that could be harmful to humans or animals One will generally desire to employ appropriate salts and buffers to render drugs, proteins or delivery vectors stable and allow for uptake by target cells. Aqueous compositions of the present disclosure comprise an effective amount of the drug, vector or proteins, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present disclosure, its use in therapeutic compositions is contemplated. Supplementary active ingredients also can be incorporated into the compositions, provided they do not inactivate the vectors or cells of the compositions.

The active compositions of the present disclosure may include classic pharmaceutical preparations. Administration of these compositions according to the present disclosure may be via any common route so long as the target tissue is available via that route. This includes oral, nasal, or buccal. Alternatively, administration may be by intradermal, subcutaneous, intramuscular, intraperitoneal or intravenous injection, or by direct injection into cardiac tissue. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present disclosure generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

VI. EXAMPLES

The following examples are included to further illustrate various aspects of the disclosure. It should be appreciated by those of skill in the art that the techniques disclosed in the examples which follow represent techniques and/or compositions discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Results

The inventors generated alanine scanning mutations across the MADS box that interact with a variety of co-accessory factors. The in vivo relevance of these sites and other conserved residues thought to be involved in SRF dependent, tissue-specific co-accessory factor interactions. They used site-directed PCR mutagenesis to create amino acid mutations at specified residues across the SRF core domain. Residues were changed to alanines (giving a neutral charge and removing potential interacting side chains). Single alanine mutations will alter many predicted DNA contact sites, and mutants that did not alter DNA binding were further evaluated. The inventors constructed five mutations of SRF with triple alanine substitutions, as shown in FIG. 1; such as SRF-141(A3), SRF-144(A3), SRF-147(A3), SRF-150(A3) and SRF-153(A3) in the N-terminal extension and part of the alpha1 coil of the MADS box, to disrupt SRF docking sites for Nkx2-5 and GATA-4.

Human SRF cDNA and mutants with N terminal HA tag were cloned into the EcoRI site of the pWPI vector, in which the inventors added an IRES-GFP tag. SRF's cooperative interactions with Nkx2.5 and GATA4 was mapped to the N-extension of the MADS box. Note the facilitated DNA binding of wild-type SRF with Gata4 (top panel of FIG. 2) and Nkx2.5 (bottom panel of FIG. 2) by Electrophoretic Mobility Assay with a [32P] labeled skeletal α-actin SRF DNA binding element called a SRE or a CArG box. In both cases the addition of Gata4 and or Nkx2.5 increases the binding of SRF as shown by the increased intensity of the shifted band. Note that SRF mutants SRF141(A3) and SRF150 (A3) did not bind the SRF binding site and failed to show a facilitated band shift. SRF mutant 144(A3) showed improved binding with and without co-factors Gata4 and or Nkx2.5. The EMSA of the SRF mutant SRF(153A3) bound to the SRF binding site but this mutation blocked facilitated binding with Gata4 and Nkx2.5.

Figure 4:
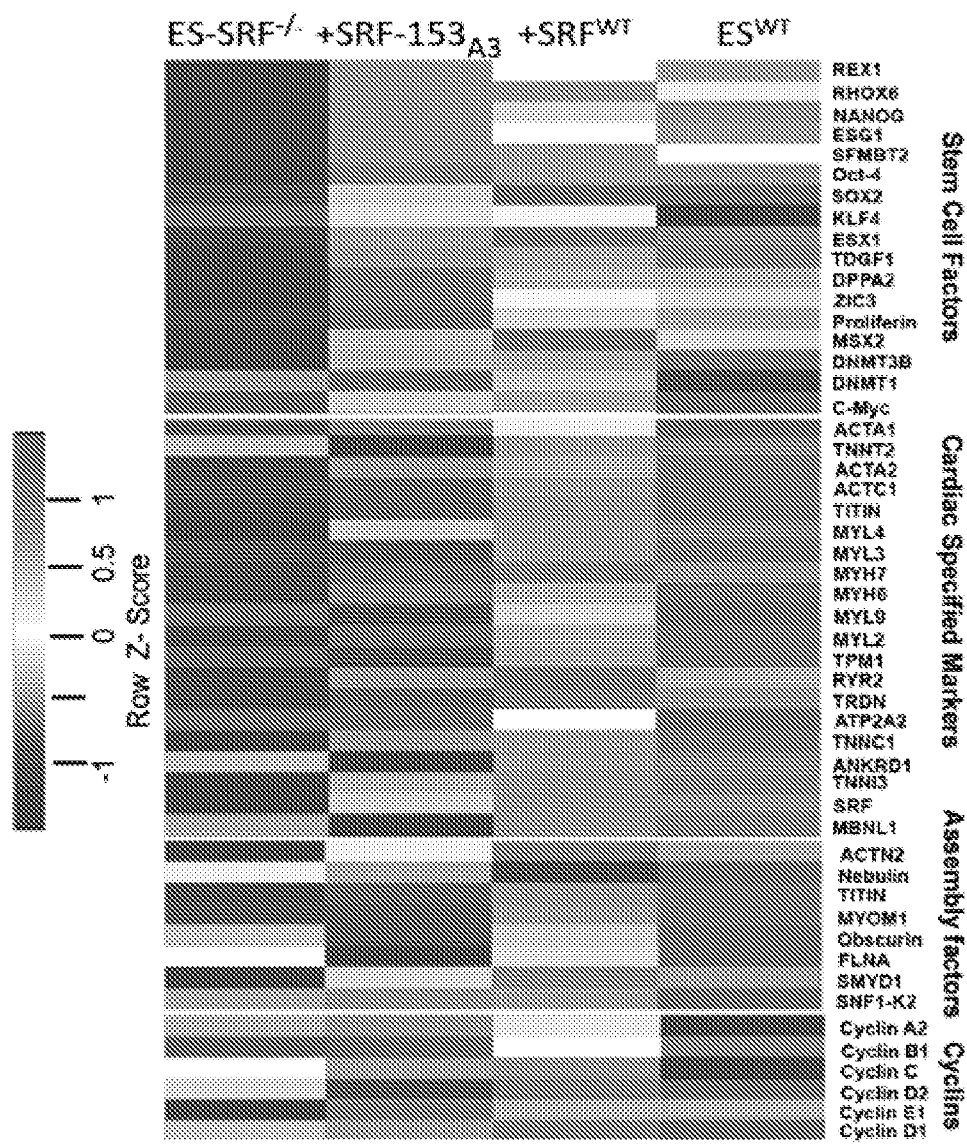
FIG. 4. Cardio-Stemin induced stem cell factors, blocked contractile proteins and assembly factors and activated cyclins. RNA samples were hybridized against Affymetrix array 430a2 chips. Analysis was done with dCHIP software (world-wide-web at dchip.org).

One of SRF mutants SRF-153($A_3$), named Cardio-Stemin, showed a powerful activation of more than 15 stem cell marker genes, such as Rex1, Nanog, Oct4, Sox2, Esg1, SFmbt2, Rhox6 and proliferin, but not Klf4 and C-Myc, in comparison to SRF null ES cells. Thus, Cardio-Stemin elicited an imperfect or partial pluripotency program. Cardio-Stemin also inhibited the induction of many cardiac myocyte specified genes such as sarcomeric actins, heavy and light chain myosins, troponins, channels and structural genes. Expression of sarcomeric assembly factors such as Actinin2, Nebulin, Titin, Myomesin, Obscurin Filamin, Smyd1 and SNF1-K2 were blocked from appearing in comparison to wild-type ES cells that formed cardiac myocytes following hanging drop formation. In addition, evidence for Cardio-Stemin for fostering cell replication was shown by the up regulation of cyclins A2, B1, C and E1 but not Cyclins D1 and D2 that are associated with terminal cell division (FIG. 4). The inventors' observation that a single transcription factor, Cardio-Stemin, albeit mutated SRF, induced expression of stem cell factors was totally unexpected and unprecedented.

Figure 5:
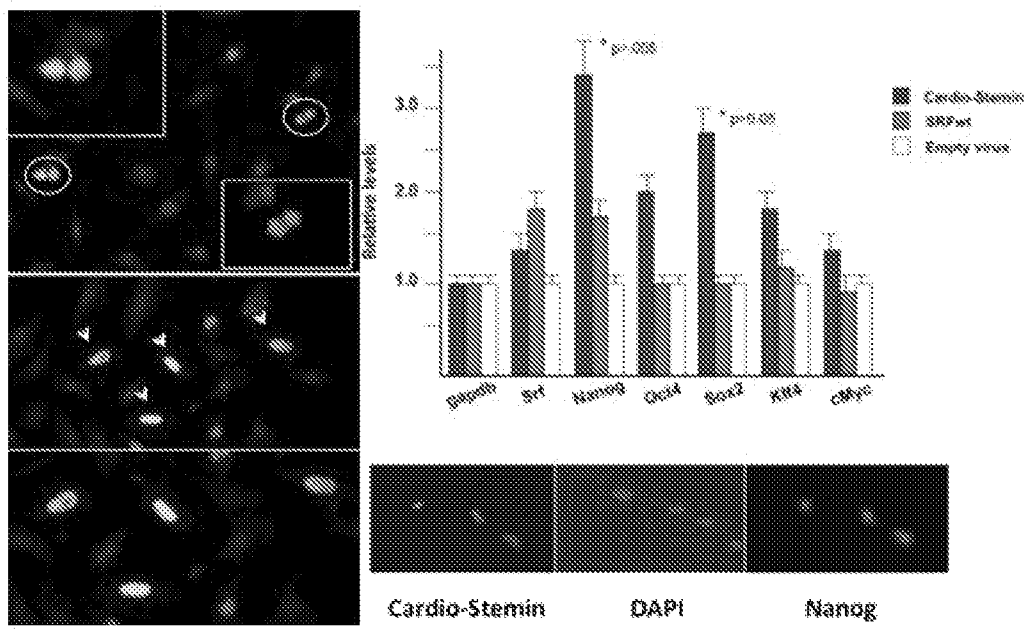
FIG. 5. showed that Cardio-Stemin infected MEFs induced cell replication, mitotic figures, Nanog and Sox2 expression Immunofluorescence staining for SRF (anti-SRF-C terminal; Santa Cruz) showed stained nuclei in replicated fibroblasts and those undergoing mitosis and the expression of Nanog with anti-Nanog (Novus Biologicals).

The inventors then asked if Cardio-Stemin would induce expression of stem cell markers in mouse embryonic fibroblasts (MEFs). They followed the protocol of Takahashi and Yamanaka to isolate MEFs from 13.5-day embryonic mice. In their study, the inventors used MEFs within three passages to avoid replicative senescence. MEFs were infected with virus-containing supernatants supplemented with polybrene. After infection, the cells were re-plated in fresh medium. Quantitative PCR analysis from RNA isolated from SRF-153 or Cardio-Stemin infected MEFs revealed the ability to drive significant levels of Nanog (3.5-fold) and Sox2 (2.7-fold). In addition, comparison to SRF-infected MEFs and empty virus-infected MEF controls cultured for 3 days showed that Cardio-Stemin infected MEFs induced Nanog and Sox2 and to a lesser extent for Oct4, Klf4 and C-myc, similar to the inventors' observations in ES cells (FIG. 2) Immunofluorescence staining for SRF (anti-SRF-C terminal; Santa Cruz) showed stained nuclei in replicated fibroblasts and those undergoing mitosis. Also, there was no pre-selection of isolated clones as done in the Takahashi and Yamanaka. The whole population of infected fibroblasts were assayed together, as an average result in FIG. 5.

Doxycyline induced lenti-viral Cardio-Stemin expression caused myocyte replication. The inventors cloned Cardio-Stemin and SRF into the Ptet-LTR1 promoter system, inducible with Doxycycline. Western immuno-staining showed robust Doxycycline induction of SRFwt and Cardio-Stemin They then tested this inducible system by Dox induction of Cardio-Stemin for short periods of time (3-days) to test whether rat cardiac myocytes purchased from Cellutron Life Technologies (Cat #ac-7031) would be reprogramed into replicating cells. Under confocal fluorescent microscopy in which controls were infected only with *Lenti*-viral rTTA, showed intact sarcomeres, DAPI stained nuclei and a lack of EdU staining. DOX induction of Cardio-Stemin showed (FIG. 6B) caused disorganized TNNT2 stained myofilaments, in comparison to control myocytes, and displayed evidence of DNA synthesis, as shown by EdU incorporation. Therefore, a pulse of Cardio-Stemin induced myocyte division, at least to the first approximation.

Synthetic Stemin mmRNA expression caused myocyte replication. Synthetic mmRNAs consist of an anti-reverse cap analog (ARCA), 5' and 3' untranslated sequences (UTRs), a polyA tail and the coding DNA of the gene of interest. Antireverse cap analog (ARCA) are modified guanosine nucleotides that are incorporated into the 5' end of the transcript and ensure that synthesis proceeds in only one direction. Capping mRNAs with ARCA simulates the natural capping process and improves transcript stability and enhances translation mmRNAs are synthesized using modified nucleotides (typically, 5-methycytidine-5'-triphosphate and pseudouridine-5'-triphosphate). These modified ribonucleotides increase transcript stability, improve translation efficiency, and decrease the innate immune response. Adding a polyA tail (a long stretch of adenine nucleotides) to the ends of transcripts during synthesis also increases transcript stability and translational efficiency mmRNAs are typically a fusion between the gene of interest's coding DNA and the 5' and 3'UTRS from a different gene such as beta-globin; the 5' and 3'UTR sequences that are typically selected are chosen because their sequences are known to increase transcript stability when they are used in place of the native UTRs of otherwise unstable transcripts.

To determine transfection efficiency, the inventors used GFP mmRNA as positive control. GFP mmRNA was mixed in ratios with Lipofectamine™ MessengerMAX™ Transfection Reagent (Thermo Fisher, LMRNA003) and transfected into rat myocyte. GFP marked cells were quantified with Image J software (NIH) and the transfection efficiency was calculated by GFP+ cell number versus DAPI cell number. FIG. 9A shows approximately 45% of the myocytes were transfected at a ratio of 0.1 μg mmRNA to 1.5 μl Lipofectamine RNA MAX™

According to the inventors' transfection protocol, as shown in FIG. 9B, Stemin mmRNA dissolved in Lipofectamine MAX™ was added twice to rat myocytes for 6 hrs over 2 days. To test whether mouse cardiac myocytes are reprogramed into replicating cells, at the end of the second day the myocytes were pulsed with alphaEdu for 6 hrs, to mark replicated myocytes by aEdu incorporation into newly synthesized DNA. Under confocal fluorescent microscopy Cardio-Stemin displayed evidence of DNA replication, as shown by EdU incorporation in about many nuclei shown in FIG. 7. Nuclei, co-stained with Edu (Red) and Dapi (Blue) shown in boxes were seen as pink in the merged images. Also, disorganized TNNT2 stained myofilaments were observed in comparison to non-transfected myocytes.

Figure 10:
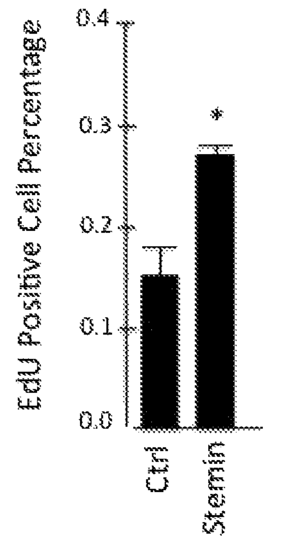
FIG. 10. The number of Edu/DAPI co-stained nuclei of TnnT marked rat cardiac myocytes. * Stands for $P<0.05$ for significance difference.
Figure 11:
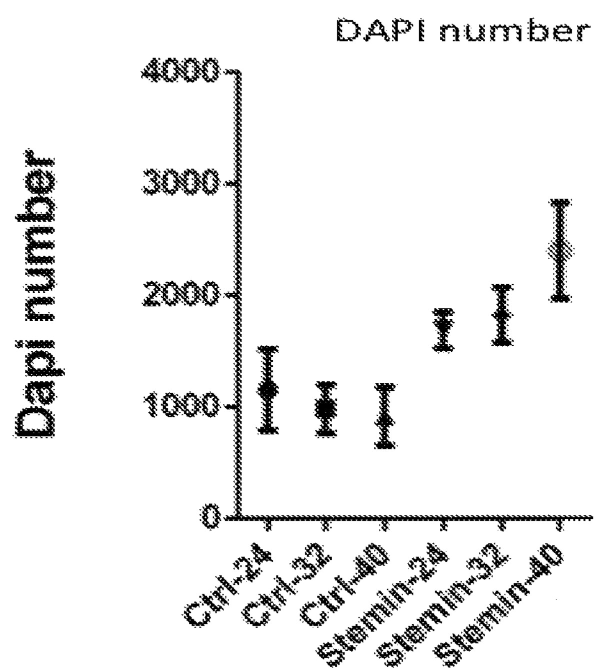
FIG. 11. Increase in number of myocytes by DAPI staining of nuclei in comparison to controls.

Next, from the same experiment thousands of transfected cardiomyocytes with Stemin mmRNA and control myocytes treated only with MLipofectamin MAX™ were quantified for their cell divisions and statistical statistically significance between the two samples with two-way ANOVA. The inventors determined that there was an approximate doubling number of myocytes stained with TnnT2 that were also labeled for Edu and stained for the nuclear stained DAPI. Thus, they validated the biological activities of Stemin of particular interest, Stemin caused cardiac myocyte to replicate (FIG. 10).

Summary Cardio-Stemin synthetic mmRNAs cause CMs to replicate in the post-MI hearts. The inventors are now developing first principles using viral transfection of cultured newborn and adult genetically marked mouse myocytes into replicating myocytes. Next, the inventors are moving their technology to synthetic RNA that could be introduced by transfectant reagents and/or nanoparticle delivery). Cardio-Stemin synthetic mmRNAs consist of an anti-reverse cap analog (ARCA), 5' and 3' untranslated sequences (UTRs), a polyA tail and the coding DNA of the gene of interest. Anti-reverse cap analog (ARCA) are modified guanosine nucleotides that are incorporated into the 5' end of the transcript and ensure that synthesis proceeds in only one direction. Capping mRNAs with ARCA simulates the natural capping process and improves transcript stability and enhances translation mmRNAs are synthesized using modified nucleotides (typically, 5-methycytidine-5'-triphosphate and pseudouridine-5'-triphosphate). These modified ribonucleotides increase transcript stability, improve translation efficiency, and decrease the innate immune response. Adding a polyA tail (a long stretch of adenine nucleotides) to the ends of transcripts during synthesis also increases transcript stability and translational efficiency mmRNAs are typically a fusion between the gene of interest's coding DNA and the 5' and 3'UTRS from a different gene such as beta-globin; the 5' and 3'UTR sequences that are typically selected are chosen because their sequences are known to increase transcript stability when they are used in place of the native UTRs of otherwise unstable transcripts. The inventors will test the untranslated regions of the skeletal alpha-actin mRNA, because of their enhanced stability and translation only in myocytes not in fibroblasts. Also, using 5' and 3'UTRs that increase mRNA stability during hypoxia would selectively stabilize mmRNA in ischemic tissue but not in healthy tissue. This limits high protein levels to only injured tissue. RNA turns over in a few days so treatment is short duration, can be multi dosed without immune consequences and does not leave a viral signature.

The loss of cardiomyocytes underlies most causes of heart failure. Normal repair processes are inadequate to deal with extensive myocardial damage. While heart transplantation is the standard for treatment, the limited availability of donor hearts and the risk of rejection restrict its widespread use. The ability to regenerate myocytes in the patient by enhanced replication with Cardio-Stemin will become the next gold standard in heart regeneration. It will replace the problematic stem cell systems. The inventors are now using synthetic RNA that could be introduced by co-transfectant reagents and/or nanoparticle delivery by a cardiac catheter may have the best chance to one day enter clinical trials and become the standard of care for treatment of adult heart disease; thus, allowing for multi-dosing without viral signatures and an immune response. The idea is to increase the number of spare myocytes from the patient's own heart to increase heart wall thickness could replace dead myocytes following an infarct or increase function in the setting of heart failure. In pediatric cardiac diseases, Cardio-Stemin may be useful to repairing congenital cardiac birth defects and expand the heart wall in hypoplastic hearts.

Because cardio-stemin can cause fibroblast replication, it's also highly likely that other target tissues and cells such as vascular smooth muscle cells, endothelial cells will be expanded and rejuvenated with Cardio-Stemin Vascular aneurysms treated with Cardio-Stemin may increas the number of vascular cells repairing the damaged vessel wall. Cell types that barely replicate post birth, such as spinal cord neurons and brain cells may also be a target for Cardio-Stemin for the repair of crushed and severed spinal cord injuries by repairing through rejuvenation and replication of motor neurons and sensory neurons. Similarly, cerebral stroke victims may be repaired by allowing Cardio-Stemin to stimulate neuron and accessory glial cells to replicate.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

Angel et al., *Cell,* 49:729, 1987a.
Angel et al., *Cell,* 49:729, 1987b.
Baharvand et al., Cell Biol. Int. 30: 800-807, 2006.
Baichwal and Sugden, In: *Gene Transfer*, Kucherlapati (Ed), NY, Plenum Press, 117-148, 1986.
Banerji et al., *Cell,* 27(2 Pt 1):299-308, 1981.
Banerji et al., *Cell,* 33(3):729-740, 1983.
Barnes et al., *J. Biol. Chem.,* 272(17):11510-7, 1997.
Belaguli et al., *Mol. Cell. Biol.* 20, 7550-7558, 2000.
Beltrami et al., Cell U 4:763-776, 2003.
Benvenisty and Neshif, *Proc. Natl. Acad. Sci. USA,* 83:9551-9555, 1986.
Berkhout et al., *Cell,* 59:273-282, 1989.
Bhaysar et al., *Genomics,* 35(1):11-23, 1996.
Blanar et al., *EMBO J.,* 8:1139, 1989.
Bodine and Ley, *EMBO J.,* 6:2997, 1987.
Boshart et al., *Cell,* 41:521, 1985.
Bosze et al., *EMBO J.,* 5(7):1615-1623, 1986.
Boxer et al., Mol. Cell. Biol. 9, 515-522, 1998.
Braddock et al., *Cell,* 58:269, 1989.
Bulla and Siddiqui, *J. Virol.,* 62:1437, 1986.
Campbell and Villarreal, *Mol. Cell. Biol.,* 8:1993, 1988.
Campere and Tilghman, *Genes and Dev.,* 3:537, 1989.
Campo et al., *Nature,* 303:77, 1983.
Capaldi et al., *Biochem. Biophys. Res. Comm.,* 74(2):425-433, 1977.
Celander and Haseltine, *J. Virology,* 61:269, 1987.
Celander et al., *J. Virology,* 62:1314, 1988.
Cen et al., *Mol. Cell. Biol,* 23, 6597-6608, 2003.
Chandler et al., *Cell,* 33:489, 1983.
Chatterjee et al., *Proc. Natl. Acad. Sci. USA,* 86:9114, 1989.
Chen and Okayama, *Mol. Cell Biol.,* 7(8):2745-2752, 1987.
Chen and Schwartz, Mol. Cell. Biol. 16:6372-6384, 1996.
Chen et al., Dev Genet. 19, 119-130, 1996a.
Choi et al., *Cell,* 53:519, 1988.
Chong et al., Nature 510: 273-277, 2014.
Coffin, In: *Virology*, Fields et al. (Eds.), Raven Press, NY, 1437-1500, 1990.
Cohen et al., *J. Cell. Physiol.,* 5:75, 1987.
Costa et al., *Mol. Cell. Biol.,* 8:81-90, 1988.
Coupar et al., *Gene,* 68:1-10, 1988.
Cripe et al., *EMBO J.,* 6:3745, 1987.
Culotta and Hamer, *Mol. Cell. Biol.,* 9:1376-1380, 1989.
Dalgleish and Sharrocks, Nucl. Acids Res. 28, 560-569, 2000.
Dalton and Treisman, Cell. 68, 597-612, 1992.
Dandolo et al., *J. Virology,* 47:55-64, 1983.
De Villiers et al., *Nature,* 312(5991):242-246, 1984.
Deschamps et al., *Science,* 230:1174-1177, 1985.
Dubensky et al., *Proc. Natl. Acad. Sci. USA,* 81:7529-7533, 1984.
Edbrooke et al., *Mol. Cell. Biol.,* 9:1908-1916, 1989.
Edlund et al., *Science,* 230:912-916, 1985.
Fechheimer et al., *Proc Natl. Acad. Sci. USA,* 84:8463-8467, 1987.
Ferkol et al., *FASEB J.,* 7:1081-1091, 1993.
Fischer, *Med. Res. Rev.,* 27(6):755-796, 2007.
Foecking and Hofstetter, *Gene,* 45(1):101-105, 1986.
Fraley et al., *Proc. Natl. Acad. Sci. USA,* 76:3348-3352, 1979.
Franz et al., *Cardoscience,* 5(4):235-43, 1994.
Friedmann, *Science,* 244:1275-1281, 1989.
Fujita et al., *Cell,* 49:357, 1987.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gilles et al., *Cell,* 33:717, 1983.
Gloss et al., *EMBO J.,* 6:3735, 1987.
Godbout et al., *Mol. Cell. Biol.,* 8:1169, 1988.
Goodbourn and Maniatis, *Proc. Natl. Acad. Sci. USA,* 85:1447, 1988.
Goodbourn et al., *Cell,* 45:601, 1986.
Gopal, *Mol. Cell Biol.,* 5:1188-1190, 1985.
Gopal-Srivastava et al., *J. Mol. Cell. Biol.,* 15(12):7081-90, 1995.
Graham and van der Eb, *Virology,* 52:456-467, 1973.
Greene et al., *Immunology Today,* 10:272, 1989

Grosschedl and Baltimore, *Cell,* 41:885, 1985.
Grunhaus and Horwitz, *Seminar in Virology,* 3:237-252, 1992.
Hare et al., JAMA 308:2369-2379. 2012
Harland and Weintraub, *J. Cell Biol.,* 101(3):1094-1099, 1985.
Haslinger and Karin, *Proc. Natl. Acad. Sci. USA,* 82:8572, 1985.
Hauber and Cullen, *J. Virology,* 62:673, 1988.
Hen et al., *Nature,* 321:249, 1986.
Hensel et al., *Lymphokine Res.,* 8:347, 1989.
Hersdorffer et al., *DNA Cell Biol.,* 9:713-723, 1990.
Hill et al., Cell. 73, 395-406, 1993.
Hirochika et al., *J. Virol.,* 61:2599, 1987.
Hitraya et al., *Arthritis Rheum.* 41(11):2048-58 1998.
Holbrook et al., *Virology,* 157:211, 1987.
Horlick and Benfield, *Mol. Cell. Biol.,* 9:2396, 1989.
Horwich et al. *J. Virol.,* 64:642-650, 1990.
Hoshina et al., *J Vasc Surg., September;* 40(3):512-8, 2004.
Huang et al., *Cell,* 27:245, 1981.
Hug et al., *Mol. Cell. Biol.,* 8:3065-3079, 1988.
Hwang et al., *Mol. Cell. Biol.,* 10:585, 1990.
Imagawa et al., *Cell,* 51:251, 1987.
Imbra and Karin, *Nature,* 323:555, 1986.
Imler et al., *Mol. Cell. Biol.,* 7:2558, 1987.
Imperiale and Nevins, *Mol. Cell. Biol.,* 4:875, 1984.
Jakobovits et al., *Mol. Cell. Biol.,* 8:2555, 1988.
Jameel and Siddiqui, *Mol. Cell. Biol.,* 6:710, 1986.
Jaynes et al., *Mol. Cell. Biol.,* 8:62, 1988.
Johnson et al., *Mol. Cell. Biol.,* 9(8):3393-3399, 1989.
Joseph et al., *Cancer Cell* 13(2):129-40, 2008.
Kadesch and Berg, *Mol. Cell. Biol.,* 6:2593, 1986.
Kaneda et al., *Science,* 243:375-378, 1989.
Karin et al., *Mol. Cell. Biol.,* 7:606, 1987.
Katinka et al., *Cell,* 20:393, 1980.
Kato et al., *J Biol Chem.,* 266(6):3361-3364, 1991.
Kattman et al., *Cell Stem Cell* 8:228-240, 2011.
Kelly et al., *J. Cell Biol.,* 129(2):383-96, 1995.
Kiledjian et al., *Mol. Cell. Biol.,* 8:145, 1988.
Kimura et al., *Dev. Growth Differ.,* 39(3):257-65, 1997.
Klamut et al., *Mol. Cell. Biol.,* 10:193, 1990.
Klein et al., *Nature,* 327:70-73, 1987.
Koch et al., *Mol. Cell. Biol.,* 9:303, 1989.
Kriegler and Botchan, *In: Eukaryotic Viral Vectors*, Gluzman (Ed.), Cold Spring Harbor: Cold Spring Harbor Laboratory, N Y, 1982.
Kriegler and Botchan, *Mol. Cell. Biol.,* 3:325, 1983.
Kriegler et al., *Cell,* 38:483, 1984a.
Kriegler et al., *Cell,* 53:45, 1988.
Kriegler et al., *In: Cancer Cells 2/Oncogenes and Viral Genes*, Van de Woude et al. eds, Cold Spring Harbor, Cold Spring Harbor Laboratory, 1984b.
Kuhl et al., *Cell,* 50:1057, 1987.
Kunz et al., *Nucl. Acids Res.,* 17:1121, 1989.
Laflamme et al., *Nat. Biotechnol.* 25:1015-1024, 2007.
LaPointe et al., *J. Biol. Chem.,* 263(19):9075-8, 1988.
Larsen et al., *Proc. Natl. Acad. Sci. USA.,* 83:8283, 1986.
Laspia et al., *Cell,* 59:283, 1989.
Latimer et al., *Mol. Cell. Biol.,* 10:760, 1990.
Laughlin et al., *J. Virol.,* 60(2):515-524, 1986.
Lebkowski et al., *Mol. Cell. Biol.,* 8(10):3988-3996, 1988.
Lee et al., *Nature,* 294:228, 1981.
Levinson et al., *Nature,* 295:79, 1982.
Li et al., J Mol Cell Cardiol, 28:1737-1746, 1996.
Lieu et al., Stem Cells Dev. 18: 1493-1500, 2009.
Lin et al., *Mol. Cell. Biol.,* 10:850, 1990.
Ling et al., J. Biol. Chem. 273, 10506-10514, 1998.
Luria et al., *EMBO J.,* 6:3307, 1987.
Lusky and Botchan, *Proc. Natl. Acad. Sci. USA,* 83:3609, 1986.
Lusky et al., *Mol. Cell. Biol.,* 3:1108, 1983.
Macejak and Sarnow, *Nature,* 353:90-94, 1991.
Majors and Varmus, *Proc. Natl. Acad. Sci. USA,* 80:5866, 1983.
Marban and Malliaras, JAMA 308:2405-2406, 2012.
Markowitz et al., *J. Virol.,* 62:1120-1124, 1988.
McDonald et al., *J. Clin. Invest.* 116, 36-48, 2006.
McLaughlin et al., *J. Virol.,* 62(6):1963-1973, 1988.
McNeall et al., *Gene,* 76:81, 1989.
Mercola et al., *Genes Dev.,* 25: 299-309, 2011.
Miksicek et al., *Cell,* 46:203, 1986.
Miralles et al., *Cell.* 113, 329-342, 2003.
Mordacq and Linzer, *Genes and Dev.,* 3:760, 1989.
Moreau et al., *Nucl. Acids Res.,* 9:6047, 1981.
Moss et al., *J. Gen. Physiol.,* 108(6):473-84, 1996.
Muesing et al., *Cell,* 48:691, 1987.
Murry et al., *J Am Coll Cardiol* 47:1777-1785, 2006.
Muzyczka, *Curr. Topics Microbiol. Immunol.,* 158:97-129, 1992.
Naldini et al., *Science,* 272(5259):263-267, 1996.
Ng et al., *Nuc. Acids Res.,* 17:601, 1989.
Nicolas and Rubinstein, Stoneham: Butterworth, pp. 494-513, 1988.
Nicolau and Sene, *Biochim. Biophys. Acta,* 721:185-190, 1982.
Nicolau et al., *Methods Enzymol.,* 149:157-176, 1987.
Niu et al., Proc Natl Acad Sci USA., 105:17824-17829, 2011.
Nurrish et al., Mol. Cell. Biol. 15, 4076-4085, 1995.
Okada et al., *American Journal of Physiology: Renal Physiology,* 275 (2): F306-F314, 1998.
Ondek et al., *EMBO J.,* 6:1017, 1987.
Ornitz et al., *Mol. Cell. Biol.,* 7:3466, 1987.
Palmiter et al., *Cell,* 29:701, 1982.
Pech et al., *Mol. Cell. Biol.,* 9:396, 1989.
Pellegrini et al., Nature. 376, 490-497, 1995.
Pelletier and Sonenberg, *Nature,* 334:320-325, 1988.
Perales et al., *Proc. Natl. Acad. Sci. USA,* 91(9):4086-4090, 1994.
Perez-Stable and Constantini, *Mol. Cell. Biol.,* 10:1116, 1990.
Physicians Desk Reference.
Picard and Schaffner, *Nature,* 307:83, 1984.
Pinkert et al., *Genes and Dev.,* 1:268, 1987.
Ponta et al., *Proc. Natl. Acad. Sci. USA,* 82:1020, 1985.
Porton et al., *Mol. Cell. Biol.,* 10:1076, 1990.
Potter et al., *Proc. Natl. Acad. Sci. USA,* 81:7161-7165, 1984.
Queen and Baltimore, *Cell,* 35:741, 1983.
Quinn et al., *Mol. Cell. Biol.,* 9:4713, 1989.
Remington's Pharmaceutical Sciences, $15^{th}$ ed., 1035-1038 and 1570-1580, Mack Publishing Company, P A, 1980.
Resendez Jr. et al., *Mol. Cell. Biol.,* 8:4579, 1988.
Ridgeway, *In: Vectors: A Survey of Molecular Cloning Vectors and Their Uses*, Rodriguez et al. (Eds.), Stoneham: Butterworth, 467-492, 1988.
Ripe et al., *Mol. Cell. Biol.,* 9:2224, 1989.
Rippe et al., *Mol. Cell Biol.,* 10:689-695, 1990.
Rittling et al., *Nuc. Acids Res.,* 17:1619, 1989.
Rosen et al., *Cell,* 41:813, 1988.
Sakai et al., *Genes and Dev.,* 2:1144, 1988.
Satake et al., *J. Virology,* 62:970, 1988.
Schaffner et al., *J. Mol. Biol.,* 201:81, 1988.
Searle et al., *Mol. Cell. Biol.,* 5:1480, 1985.

Sepulveda et al., J. Biol. Chem. 277, 25775-25782, 2002.
Sharrocks and Shore, Nucl. Acids. Res 23, 2442-2449, 1995.
Sharrocks et al., Mol. Cell. Biol. 13, 123-132, 1993a.
Sharrocks et al., Nucl. Acids. Res, 21, 215-221, 1993b.
Shaul and Ben-Levy, *EMBO J.,* 6:1913, 1987.
Sherman et al., *Mol. Cell. Biol.,* 9:50, 1989.
Shore and Sharrocks, Eur. J. biochem. 229, 1-13, 1995.
Shore et al., Mol. Cell. Biol. 14, 3283-3291, 1994.
Sleigh and Lockett, *J. EMBO,* 4:3831, 1985.
Spalholz et al., *Cell,* 42:183, 1985.
Spandau and Lee, *J. Virology,* 62:427, 1988.
Spandidos and Wilkie, *EMBO J.,* 2:1193, 1983.
Srivastava and Olson, Trends Cell Biol; 7:447-453, 1995.
Stephens and Hentschel, *Biochem. J.,* 248:1, 1987.
Stuart et al., *Nature,* 317:828, 1985.
Sullivan and Peterlin, *Mol. Cell. Biol,* 7:3315, 1987.
Swartzendruber and Lehman, *J. Cell. Physiology,* 85:179, 1975.
Takahashi et al., *Antibiotics,* 49:453, 1996.
Takebe et al., *Mol. Cell. Biol.,* 8:466, 1988.
Tavernier et al., *Nature,* 301:634, 1983.
Taylor and Kingston, *Mol. Cell. Biol.,* 10:165, 1990a.
Taylor and Kingston, *Mol. Cell. Biol.,* 10:176, 1990b.
Taylor et al., *J. Biol. Chem.,* 264:15160, 1989.
The Merck Index, 11th Edition.
Thiesen et al., *J. Virology,* 62:614, 1988.
Tratschin et al., *Mol. Cell. Biol.,* 4:2072-2081, 1984.
Treisman, Cancer Biol. 1, 47-58, 1990.
Treisman, Curr. Opin. Genet. Dev 4, 96-101, 1994.
Treisman, EMBO. J. 14, 4905-4913, 1995.
Tronche et al., *Mol. Biol. Med.,* 7:173, 1990.
Tronche et al., *Mol. Cell. Biol.,* 9:4759, 1989.
Trudel and Constantini, *Genes and Dev.,* 6:954, 1987.
Tur-Kaspa et al., *Mol. Cell Biol.,* 6:716-718, 1986.
U.S. Pat. No. 4,797,368
U.S. Pat. No. 5,139,941
U.S. Pat. No. 5,994,136
U.S. Pat. No. 6,013,516
Vannice and Levinson, *J. Virology,* 62:1305, 1988.
Varmus et al., *Cell,* 25:23-36, 1981.
Vasseur et al., *Proc Natl. Acad. Sci. U.S.A.,* 77:1068, 1980.
Wagner et al., *Proc. Natl. Acad. Sci. USA* 87(9):3410-3414, 1990.
Wang and Zhang, *Cell Tissue Res*., Nov. 23, 2017.
Wang et al., Cell 105, 851-862, 20001.
Wang et al., Nature. 428, 185-189, 2004.
Wang et al., Proc. Natl. Acad. Sci. USA. 99, 14855-14860, 2002.
Weber et al., *Cell,* 36:983, 1984.
Weinberger et al. *Mol. Cell. Biol.,* 8:988, 1984.
West and Sharrocks, J. Mol. Biol. 286, 1311-1323, 1999.
West et al., Mol. Cell. Biol. 17, 2876-2887, 1995.
Wong et al., *Gene,* 10:87-94, 1980.
Wu and Wu, *Adv. Drug Delivery Rev.,* 12:159-167, 1993.
Wu and Wu, *Biochemistry,* 27: 887-892, 1988.
Wu and Wu, *J. Biol. Chem.,* 262:4429-4432, 1987.
Yamauchi-Takihara et al., *Proc. Natl. Acad. Sci. USA,* 86(10):3504-3508, 1989.
Yang et al., *Proc. Natl. Acad. Sci. USA,* 87:9568-9572, 1990.
Young et al., In: *Handbook of Applied Therapeutics,* 7.1-7.12 and 9.1-9.10, 1989.
Yutzey et al. *Mol. Cell. Biol.,* 9:1397, 1989.
Zaromytidou et al., Mol. Cell. Biol. 26, 4134-4148, 2006.
Zelenin et al., *FEBS Lett.,* 280:94-96, 1991.
Zhang et al., Circ Res. 104:e30-e41, 2009.
Ziober and Kramer, *J. Bio. Chem.,* 271(37):22915-22922, 1996.
Zufferey et al., *Nat. Biotechnol.,* 15(9):871-875, 1997.

What is claimed is:

1. A method of inducing cardiomyocyte de-differentiation comprising providing to a target cardiomyocyte a STEMIN-encoding mRNA, wherein said RNA encodes a polypeptide comprising at least 22 consecutive residues of the sequence SGAKPGKKTRGRVKIKMEFIDNKLRRYTTFSKRKTGIMKKAYELSTLT (SEQ ID NO: 1) and a triple alanine substitution in region of KMEFIDN (SEQ ID NO: 2).

2. The method of claim 1, wherein providing comprises delivering a STEMIN-encoding mRNA to said target cell.

3. The method of claim 1, wherein said STEMIN-encoding RNA is bound to a nanoparticle.

4. The method of claim 3, wherein said STEMIN-encoding RNA comprise one or more modified nucleotides, such as 5-methycytidine-5'-triphosphate and/or pseudouridine-5'-triphosphate.

5. A method of inducing cardiomyocyte de-differentiation in a subject comprising providing to a target cardiomyocyte in said subject a STEMIN-encoding mRNA, wherein said RNA encodes a polypeptide comprising at least 22 consecutive residues of the sequence SGAKPGKKTRGRVKIKMEFIDNKLRRYTTFSKRKTGIMKKAYELSTLT (SEQ ID NO: 1) and a triple alanine substitution in region of KMEFIDN (SEQ ID NO: 2).

6. The method of claim 5, wherein providing comprises delivering a STEMIN-encoding mRNA to said target cardiomyocyte.

7. The method of claim 5, wherein said STEMIN-encoding RNA is bound to a nanoparticle.

8. The method of claim 7, wherein said STEMIN-encoding RNA comprise one or more modified nucleotides, such as 5-methycytidine-5'-triphosphate and/or pseudouridine-5'-triphosphate.

9. The method of claim 5, wherein said subject suffers from heart failure.

10. A method preventing or delaying development of cardiac hypertrophy or heart failure in a subject having suffered a myocardial infarct (MI) comprising providing to said subject a STEMIN-encoding mRNA, wherein said RNA encodes a polypeptide comprising at least 22 consecutive residues of the sequence SGAKPGKKTRGRVKIKMEFIDNKLRRYTTFSKRKTGIMKKAYELSTLT (SEQ ID NO: 1) and a triple alanine substitution in region of KMEFIDN (SEQ ID NO: 2).

11. The method of claim 10, wherein preventing or delaying comprises preventing or delaying cardiac hypertrophy.

12. The method of claim 10, wherein preventing or delaying comprises preventing or delaying one or more of decreased exercise capacity, decreased cardiac ejection volume, increased left ventricular end diastolic pressure, increased pulmonary capillary wedge pressure, decreased cardiac output or cardiac index, increased pulmonary artery pressures, increased left ventricular end systolic and diastolic dimensions, increased left and right ventricular wall stress, increased wall tension, decreased quality of life, and/or increased disease related morbidity or mortality.

13. The method of claim 10, wherein STEMIN-encoding mRNAs are administered to said subject.

14. A method of reducing a decrease in exercise tolerance and/or improving quality of life of a subject having suffered a myocardial infarction comprising providing to said subject a STEMINs-encoding mRNA, wherein said RNA encodes a polypeptide comprising at least 22 consecutive residues of the sequence SGAKPGKKTRGRVKIKMEFIDNKLRRYTTFSKRKTGIMKKAYELSTLT (SEQ ID NO: 1) and a triple alanine substitution in region of KMEFIDN (SEQ ID NO: 2).

15. A polypeptide comprising at least 22 consecutive residues of the sequence SGAKPGKKTRGRVKIKMEFIDNKLRRYTTFSKRKTGIMKKAYELSTLT (SEQ ID NO: 1) and a triple alanine substitution in region of KMEFIDN (SEQ ID NO: 2).

16. A polypeptide comprising the sequence of PGKKTRGRVKIAAAFIDNKL (SEQ ID NO: 56).

17. A polypeptide comprising the sequence of PGKKTRGRVKIKMEFIDAAA (SEQ ID NO: 58).

18. The method of claim 1, wherein the polypeptide comprises the sequence of PGKKTRGRVKIAAAFIDNKL (SEQ ID NO: 56).

19. The method of claim 1, wherein the polypeptide comprises the sequence of PGKKTRGRVKIKMEFIDAAA (SEQ ID NO: 58).

* * * * *

SEQUENCE LISTING

```
<160> NUMBER OF SEQ ID NOS: 58

<210> SEQ ID NO 1
<211> LENGTH: 48
<212> TYPE: PRT
<213> ORGANISM: Artificial sequence
<220> FEATURE:
<223> OTHER INFORMATION: Synthetic polypeptide

<400> SEQUENCE: 1

Ser Gly Ala Lys Pro Gly Lys Lys Thr Arg Gly Arg Val Lys Ile Lys
1               5                   10                  15

Met Glu Phe Ile Asp Asn Lys Leu Arg Arg Tyr Thr Thr Phe Ser Lys
            20                  25                  30

Arg Lys Thr Gly Ile Met Lys Lys Ala Tyr Glu Leu Ser Thr Leu Thr
        35                  40                  45


<210> SEQ ID NO 2
<211> LENGTH: 7
<212> TYPE: PRT
<213> ORGANISM: Artificial sequence
<220> FEATURE:
<223> OTHER INFORMATION: Synthetic peptide

<400> SEQUENCE: 2

Lys Met Glu Phe Ile Asp Asn
1               5


<210> SEQ ID NO 3
```

```
<211> LENGTH: 508
<212> TYPE: PRT
<213> ORGANISM: Artificial sequence
<220> FEATURE:
<223> OTHER INFORMATION: Synthetic polypeptide

<400> SEQUENCE: 3

Met Leu Pro Thr Gln Ala Gly Ala Ala Ala Ala Leu Gly Arg Gly Ser
1               5                   10                  15

Ala Leu Gly Gly Ser Leu Asn Arg Thr Pro Thr Gly Arg Pro Gly Gly
            20                  25                  30

Gly Gly Gly Thr Arg Gly Ala Asn Gly Gly Arg Val Pro Gly Asn Gly
        35                  40                  45

Ala Gly Leu Gly Pro Gly Arg Leu Glu Arg Glu Ala Ala Ala Ala Ala
    50                  55                  60

Ala Thr Thr Pro Ala Pro Thr Ala Gly Ala Leu Tyr Ser Gly Ser Glu
65                  70                  75                  80

Gly Asp Ser Glu Ser Gly Glu Glu Glu Glu Leu Gly Ala Glu Arg Arg
                85                  90                  95

Gly Leu Lys Arg Ser Leu Ser Glu Met Glu Ile Gly Met Val Val Gly
            100                 105                 110

Gly Pro Glu Ala Ser Ala Ala Ala Thr Gly Gly Tyr Gly Pro Val Ser
        115                 120                 125

Gly Ala Val Ser Gly Ala Lys Pro Gly Lys Lys Thr Arg Gly Arg Val
    130                 135                 140

Lys Ile Lys Met Glu Phe Ile Asp Asn Lys Leu Arg Arg Tyr Thr Thr
145                 150                 155                 160

Phe Ser Lys Arg Lys Thr Gly Ile Met Lys Lys Ala Tyr Glu Leu Ser
                165                 170                 175

Thr Leu Thr Gly Thr Gln Val Leu Leu Leu Val Ala Ser Glu Thr Gly
            180                 185                 190

His Val Tyr Thr Phe Ala Thr Arg Lys Leu Gln Pro Met Ile Thr Ser
        195                 200                 205

Glu Thr Gly Lys Ala Leu Ile Gln Thr Cys Leu Asn Ser Pro Asp Ser
    210                 215                 220

Pro Pro Arg Ser Asp Pro Thr Thr Asp Gln Arg Met Ser Ala Thr Gly
225                 230                 235                 240

Phe Glu Glu Thr Asp Leu Thr Tyr Gln Val Ser Glu Ser Asp Ser Ser
                245                 250                 255

Gly Glu Thr Lys Asp Thr Leu Lys Pro Ala Phe Thr Val Thr Asn Leu
            260                 265                 270

Pro Gly Thr Thr Ser Thr Ile Gln Thr Ala Pro Ser Thr Ser Thr Thr
        275                 280                 285

Met Gln Val Ser Ser Gly Pro Ser Phe Pro Ile Thr Asn Tyr Leu Ala
    290                 295                 300

Pro Val Ser Ala Ser Val Ser Pro Ser Ala Val Ser Ser Ala Asn Gly
305                 310                 315                 320

Thr Val Leu Lys Ser Thr Gly Ser Gly Pro Val Ser Ser Gly Gly Leu
                325                 330                 335

Met Gln Leu Pro Thr Ser Phe Thr Leu Met Pro Gly Gly Ala Val Ala
            340                 345                 350

Gln Gln Val Pro Val Gln Ala Ile Gln Val His Gln Ala Pro Gln Gln
        355                 360                 365

Ala Ser Pro Ser Arg Asp Ser Ser Thr Asp Leu Thr Gln Thr Ser Ser
    370                 375                 380
```

```
Ser Gly Thr Val Thr Leu Pro Ala Thr Ile Met Thr Ser Ser Val Pro
385                 390                 395                 400

Thr Thr Val Gly Gly His Met Met Tyr Pro Ser Pro His Ala Val Met
                405                 410                 415

Tyr Ala Pro Thr Ser Gly Leu Gly Asp Gly Ser Leu Thr Val Leu Asn
            420                 425                 430

Ala Phe Ser Gln Ala Pro Ser Thr Met Gln Val Ser His Ser Gln Val
        435                 440                 445

Gln Glu Pro Gly Gly Val Pro Gln Val Phe Leu Thr Ala Ser Ser Gly
    450                 455                 460

Thr Val Gln Ile Pro Val Ser Ala Val Gln Leu His Gln Met Ala Val
465                 470                 475                 480

Ile Gly Gln Gln Ala Gly Ser Ser Ser Asn Leu Thr Glu Leu Gln Val
                485                 490                 495

Val Asn Leu Asp Thr Ala His Ser Thr Lys Ser Glu
            500                 505


<210> SEQ ID NO 4
<211> LENGTH: 92
<212> TYPE: PRT
<213> ORGANISM: Artificial sequence
<220> FEATURE:
<223> OTHER INFORMATION: Synthetic polypeptide

<400> SEQUENCE: 4

Ser Gly Ala Lys Pro Gly Lys Lys Thr Arg Gly Arg Val Lys Ile Lys
1               5                   10                  15

Met Glu Phe Ile Asp Asn Lys Leu Arg Arg Tyr Thr Thr Phe Ser Lys
            20                  25                  30

Arg Lys Thr Gly Ile Met Lys Lys Ala Tyr Glu Leu Ser Thr Leu Thr
        35                  40                  45

Gly Thr Gln Val Leu Leu Leu Val Ala Ser Glu Thr Gly His Val Tyr
    50                  55                  60

Thr Phe Ala Thr Arg Lys Leu Gln Pro Met Ile Thr Ser Glu Thr Gly
65                  70                  75                  80

Lys Ala Leu Ile Gln Thr Cys Leu Asn Ser Pro Asp
                85                  90


<210> SEQ ID NO 5
<211> LENGTH: 508
<212> TYPE: PRT
<213> ORGANISM: Artificial sequence
<220> FEATURE:
<223> OTHER INFORMATION: Synthetic polypeptide

<400> SEQUENCE: 5

Met Leu Pro Thr Gln Ala Gly Ala Ala Ala Ala Leu Gly Arg Gly Ser
1               5                   10                  15

Ala Leu Gly Gly Ser Leu Asn Arg Thr Pro Thr Gly Arg Pro Gly Gly
            20                  25                  30

Gly Gly Gly Thr Arg Gly Ala Asn Gly Gly Arg Val Pro Gly Asn Gly
        35                  40                  45

Ala Gly Leu Gly Pro Gly Arg Leu Glu Arg Glu Ala Ala Ala Ala Ala
    50                  55                  60

Ala Thr Thr Pro Ala Pro Thr Ala Gly Ala Leu Tyr Ser Gly Ser Glu
65                  70                  75                  80

Gly Asp Ser Glu Ser Gly Glu Glu Glu Glu Leu Gly Ala Glu Arg Arg
```

-continued

```
                85                  90                  95

Gly Leu Lys Arg Ser Leu Ser Glu Met Glu Ile Gly Met Val Val Gly
            100                 105                 110

Gly Pro Glu Ala Ser Ala Ala Ala Thr Gly Gly Tyr Gly Pro Val Ser
        115                 120                 125

Gly Ala Val Ser Gly Ala Lys Pro Gly Lys Lys Thr Arg Gly Arg Val
    130                 135                 140

Lys Ile Lys Met Glu Phe Ile Asp Ala Ala Ala Arg Arg Tyr Thr Thr
145                 150                 155                 160

Phe Ser Lys Arg Lys Thr Gly Ile Met Lys Lys Ala Tyr Glu Leu Ser
                165                 170                 175

Thr Leu Thr Gly Thr Gln Val Leu Leu Leu Val Ala Ser Glu Thr Gly
            180                 185                 190

His Val Tyr Thr Phe Ala Thr Arg Lys Leu Gln Pro Met Ile Thr Ser
        195                 200                 205

Glu Thr Gly Lys Ala Leu Ile Gln Thr Cys Leu Asn Ser Pro Asp Ser
    210                 215                 220

Pro Pro Arg Ser Asp Pro Thr Thr Asp Gln Arg Met Ser Ala Thr Gly
225                 230                 235                 240

Phe Glu Glu Thr Asp Leu Thr Tyr Gln Val Ser Glu Ser Asp Ser Ser
                245                 250                 255

Gly Glu Thr Lys Asp Thr Leu Lys Pro Ala Phe Thr Val Thr Asn Leu
            260                 265                 270

Pro Gly Thr Thr Ser Thr Ile Gln Thr Ala Pro Ser Thr Ser Thr Thr
        275                 280                 285

Met Gln Val Ser Ser Gly Pro Ser Phe Pro Ile Thr Asn Tyr Leu Ala
    290                 295                 300

Pro Val Ser Ala Ser Val Ser Pro Ser Ala Val Ser Ser Ala Asn Gly
305                 310                 315                 320

Thr Val Leu Lys Ser Thr Gly Ser Gly Pro Val Ser Ser Gly Gly Leu
                325                 330                 335

Met Gln Leu Pro Thr Ser Phe Thr Leu Met Pro Gly Gly Ala Val Ala
            340                 345                 350

Gln Gln Val Pro Val Gln Ala Ile Gln Val His Gln Ala Pro Gln Gln
        355                 360                 365

Ala Ser Pro Ser Arg Asp Ser Ser Thr Asp Leu Thr Gln Thr Ser Ser
    370                 375                 380

Ser Gly Thr Val Thr Leu Pro Ala Thr Ile Met Thr Ser Ser Val Pro
385                 390                 395                 400

Thr Thr Val Gly Gly His Met Met Tyr Pro Ser Pro His Ala Val Met
                405                 410                 415

Tyr Ala Pro Thr Ser Gly Leu Gly Asp Gly Ser Leu Thr Val Leu Asn
            420                 425                 430

Ala Phe Ser Gln Ala Pro Ser Thr Met Gln Val Ser His Ser Gln Val
        435                 440                 445

Gln Glu Pro Gly Gly Val Pro Gln Val Phe Leu Thr Ala Ser Ser Gly
    450                 455                 460

Thr Val Gln Ile Pro Val Ser Ala Val Gln Leu His Gln Met Ala Val
465                 470                 475                 480

Ile Gly Gln Gln Ala Gly Ser Ser Ser Asn Leu Thr Glu Leu Gln Val
                485                 490                 495

Val Asn Leu Asp Thr Ala His Ser Thr Lys Ser Glu
            500                 505
```

<210> SEQ ID NO 6
<211> LENGTH: 508
<212> TYPE: PRT
<213> ORGANISM: Artificial sequence
<220> FEATURE:
<223> OTHER INFORMATION: Synthetic polypeptide

<400> SEQUENCE: 6

```
Met Leu Pro Thr Gln Ala Gly Ala Ala Ala Ala Leu Gly Arg Gly Ser
1               5                   10                  15

Ala Leu Gly Gly Ser Leu Asn Arg Thr Pro Thr Gly Arg Pro Gly Gly
            20                  25                  30

Gly Gly Gly Thr Arg Gly Ala Asn Gly Gly Arg Val Pro Gly Asn Gly
        35                  40                  45

Ala Gly Leu Gly Pro Gly Arg Leu Glu Arg Glu Ala Ala Ala Ala Ala
    50                  55                  60

Ala Thr Thr Pro Ala Pro Thr Ala Gly Ala Leu Tyr Ser Gly Ser Glu
65                  70                  75                  80

Gly Asp Ser Glu Ser Gly Glu Glu Glu Glu Leu Gly Ala Glu Arg Arg
                85                  90                  95

Gly Leu Lys Arg Ser Leu Ser Glu Met Glu Ile Gly Met Val Val Gly
            100                 105                 110

Gly Pro Glu Ala Ser Ala Ala Ala Thr Gly Gly Tyr Gly Pro Val Ser
        115                 120                 125

Gly Ala Val Ser Gly Ala Lys Pro Gly Lys Lys Thr Arg Gly Arg Val
    130                 135                 140

Lys Ile Ala Ala Ala Phe Ile Asp Asn Lys Leu Arg Arg Tyr Thr Thr
145                 150                 155                 160

Phe Ser Lys Arg Lys Thr Gly Ile Met Lys Lys Ala Tyr Glu Leu Ser
                165                 170                 175

Thr Leu Thr Gly Thr Gln Val Leu Leu Leu Val Ala Ser Glu Thr Gly
            180                 185                 190

His Val Tyr Thr Phe Ala Thr Arg Lys Leu Gln Pro Met Ile Thr Ser
        195                 200                 205

Glu Thr Gly Lys Ala Leu Ile Gln Thr Cys Leu Asn Ser Pro Asp Ser
    210                 215                 220

Pro Pro Arg Ser Asp Pro Thr Thr Asp Gln Arg Met Ser Ala Thr Gly
225                 230                 235                 240

Phe Glu Glu Thr Asp Leu Thr Tyr Gln Val Ser Glu Ser Asp Ser Ser
                245                 250                 255

Gly Glu Thr Lys Asp Thr Leu Lys Pro Ala Phe Thr Val Thr Asn Leu
            260                 265                 270

Pro Gly Thr Thr Ser Thr Ile Gln Thr Ala Pro Ser Thr Ser Thr Thr
        275                 280                 285

Met Gln Val Ser Ser Gly Pro Ser Phe Pro Ile Thr Asn Tyr Leu Ala
    290                 295                 300

Pro Val Ser Ala Ser Val Ser Pro Ser Ala Val Ser Ser Ala Asn Gly
305                 310                 315                 320

Thr Val Leu Lys Ser Thr Gly Ser Gly Pro Val Ser Ser Gly Gly Leu
                325                 330                 335

Met Gln Leu Pro Thr Ser Phe Thr Leu Met Pro Gly Gly Ala Val Ala
            340                 345                 350

Gln Gln Val Pro Val Gln Ala Ile Gln Val His Gln Ala Pro Gln Gln
        355                 360                 365
```

```
Ala Ser Pro Ser Arg Asp Ser Ser Thr Asp Leu Thr Gln Thr Ser Ser
    370                 375                 380

Ser Gly Thr Val Thr Leu Pro Ala Thr Ile Met Thr Ser Ser Val Pro
385                 390                 395                 400

Thr Thr Val Gly Gly His Met Met Tyr Pro Ser Pro His Ala Val Met
                405                 410                 415

Tyr Ala Pro Thr Ser Gly Leu Gly Asp Gly Ser Leu Thr Val Leu Asn
            420                 425                 430

Ala Phe Ser Gln Ala Pro Ser Thr Met Gln Val Ser His Ser Gln Val
        435                 440                 445

Gln Glu Pro Gly Gly Val Pro Gln Val Phe Leu Thr Ala Ser Ser Gly
    450                 455                 460

Thr Val Gln Ile Pro Val Ser Ala Val Gln Leu His Gln Met Ala Val
465                 470                 475                 480

Ile Gly Gln Gln Ala Gly Ser Ser Ser Asn Leu Thr Glu Leu Gln Val
                485                 490                 495

Val Asn Leu Asp Thr Ala His Ser Thr Lys Ser Glu
            500                 505
```

<210> SEQ ID NO 7

<400> SEQUENCE: 7

000

<210> SEQ ID NO 8

<400> SEQUENCE: 8

000

<210> SEQ ID NO 9
<211> LENGTH: 23
<212> TYPE: PRT
<213> ORGANISM: Artificial sequence
<220> FEATURE:
<223> OTHER INFORMATION: Synthetic peptide

<400> SEQUENCE: 9

```
Gly Ala Leu Phe Leu Gly Trp Leu Gly Ala Ala Gly Ser Thr Met Gly
1               5                   10                  15

Ala Lys Lys Lys Arg Lys Val
            20
```

<210> SEQ ID NO 10
<211> LENGTH: 16
<212> TYPE: PRT
<213> ORGANISM: Artificial sequence
<220> FEATURE:
<223> OTHER INFORMATION: Synthetic peptide

<400> SEQUENCE: 10

```
Arg Gln Ile Lys Ile Trp Phe Gln Asn Arg Arg Met Lys Trp Lys Lys
1               5                   10                  15
```

<210> SEQ ID NO 11
<211> LENGTH: 7
<212> TYPE: PRT
<213> ORGANISM: Artificial sequence
<220> FEATURE:
<223> OTHER INFORMATION: Synthetic peptide

<400> SEQUENCE: 11

```
Arg Arg Met Lys Trp Lys Lys
1               5
```

<210> SEQ ID NO 12
<211> LENGTH: 16
<212> TYPE: PRT
<213> ORGANISM: Artificial sequence
<220> FEATURE:
<223> OTHER INFORMATION: Synthetic peptide

<400> SEQUENCE: 12

```
Arg Arg Trp Arg Arg Trp Trp Arg Arg Trp Trp Arg Arg Trp Arg Arg
1               5                   10                  15
```

<210> SEQ ID NO 13
<211> LENGTH: 18
<212> TYPE: PRT
<213> ORGANISM: Artificial sequence
<220> FEATURE:
<223> OTHER INFORMATION: Synthetic peptide

<400> SEQUENCE: 13

```
Arg Gly Gly Arg Leu Ser Tyr Ser Arg Arg Arg Phe Ser Thr Ser Thr
1               5                   10                  15

Gly Arg
```

<210> SEQ ID NO 14
<211> LENGTH: 11
<212> TYPE: PRT
<213> ORGANISM: Artificial sequence
<220> FEATURE:
<223> OTHER INFORMATION: Synthetic peptide

<400> SEQUENCE: 14

```
Tyr Gly Arg Lys Lys Arg Arg Gln Arg Arg Arg
1               5                   10
```

<210> SEQ ID NO 15
<211> LENGTH: 9
<212> TYPE: PRT
<213> ORGANISM: Artificial sequence
<220> FEATURE:
<223> OTHER INFORMATION: Synthetic peptide

<400> SEQUENCE: 15

```
Arg Lys Lys Arg Arg Gln Arg Arg Arg
1               5
```

<210> SEQ ID NO 16
<211> LENGTH: 11
<212> TYPE: PRT
<213> ORGANISM: Artificial sequence
<220> FEATURE:
<223> OTHER INFORMATION: Synthetic peptide

<400> SEQUENCE: 16

```
Tyr Ala Arg Ala Ala Ala Arg Gln Ala Arg Ala
1               5                   10
```

<210> SEQ ID NO 17
<211> LENGTH: 8
<212> TYPE: PRT
<213> ORGANISM: Artificial sequence
<220> FEATURE:
<223> OTHER INFORMATION: Synthetic peptide

<400> SEQUENCE: 17

```
Arg Arg Arg Arg Arg Arg Arg Arg
1               5
```

<210> SEQ ID NO 18
<211> LENGTH: 8
<212> TYPE: PRT
<213> ORGANISM: Artificial sequence
<220> FEATURE:
<223> OTHER INFORMATION: Synthetic peptide

<400> SEQUENCE: 18

```
Lys Lys Lys Lys Lys Lys Lys Lys
1               5
```

<210> SEQ ID NO 19
<211> LENGTH: 27
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (25)..(25)
<223> OTHER INFORMATION: Xaa can be any naturally occurring amino acid

<400> SEQUENCE: 19

```
Gly Trp Thr Leu Asn Ser Ala Gly Tyr Leu Leu Gly Lys Ile Asn Leu
1               5                   10                  15

Lys Ala Leu Ala Ala Leu Ala Lys Xaa Ile Leu
            20                  25
```

<210> SEQ ID NO 20
<211> LENGTH: 18
<212> TYPE: PRT
<213> ORGANISM: Artificial sequence
<220> FEATURE:
<223> OTHER INFORMATION: Synthetic peptide

<400> SEQUENCE: 20

```
Leu Leu Ile Leu Leu Arg Arg Arg Ile Arg Lys Gln Ala Asn Ala His
1               5                   10                  15

Ser Lys
```

<210> SEQ ID NO 21
<211> LENGTH: 16
<212> TYPE: PRT
<213> ORGANISM: Artificial sequence
<220> FEATURE:
<223> OTHER INFORMATION: Synthetic peptide

<400> SEQUENCE: 21

```
Ser Arg Arg His His Cys Arg Ser Lys Ala Lys Arg Ser Arg His His
1               5                   10                  15
```

<210> SEQ ID NO 22
<211> LENGTH: 11
<212> TYPE: PRT
<213> ORGANISM: Artificial sequence
<220> FEATURE:
<223> OTHER INFORMATION: Synthetic peptide

<400> SEQUENCE: 22

```
Asn Arg Ala Arg Arg Asn Arg Arg Arg Val Arg
1               5                   10
```

<210> SEQ ID NO 23
<211> LENGTH: 15
<212> TYPE: PRT
<213> ORGANISM: Artificial sequence
<220> FEATURE:
<223> OTHER INFORMATION: Synthetic peptide

<400> SEQUENCE: 23

Arg Gln Leu Arg Ile Ala Gly Arg Arg Leu Arg Gly Arg Ser Arg
1 5 10 15

<210> SEQ ID NO 24
<211> LENGTH: 13
<212> TYPE: PRT
<213> ORGANISM: Artificial sequence
<220> FEATURE:
<223> OTHER INFORMATION: Synthetic peptide

<400> SEQUENCE: 24

Lys Leu Ile Lys Gly Arg Thr Pro Ile Lys Phe Gly Lys
1 5 10

<210> SEQ ID NO 25
<211> LENGTH: 10
<212> TYPE: PRT
<213> ORGANISM: Artificial sequence
<220> FEATURE:
<223> OTHER INFORMATION: Synthetic peptide

<400> SEQUENCE: 25

Arg Arg Ile Pro Asn Arg Arg Pro Arg Arg
1 5 10

<210> SEQ ID NO 26
<211> LENGTH: 18
<212> TYPE: PRT
<213> ORGANISM: Artificial sequence
<220> FEATURE:
<223> OTHER INFORMATION: Synthetic peptide

<400> SEQUENCE: 26

Lys Leu Ala Leu Lys Leu Ala Leu Lys Ala Leu Lys Ala Ala Leu Lys
1 5 10 15

Leu Ala

<210> SEQ ID NO 27
<211> LENGTH: 14
<212> TYPE: PRT
<213> ORGANISM: Artificial sequence
<220> FEATURE:
<223> OTHER INFORMATION: Synthetic peptide

<400> SEQUENCE: 27

Lys Leu Ala Lys Leu Ala Lys Lys Leu Ala Lys Leu Ala Lys
1 5 10

<210> SEQ ID NO 28
<211> LENGTH: 27
<212> TYPE: PRT
<213> ORGANISM: Artificial sequence
<220> FEATURE:
<223> OTHER INFORMATION: Synthetic peptide

<400> SEQUENCE: 28

Gly Ala Leu Phe Leu Gly Phe Leu Gly Ala Ala Gly Ser Thr Asn Gly

```
1               5                   10                  15

Ala Trp Ser Gln Pro Lys Lys Lys Arg Lys Val
            20                  25


<210> SEQ ID NO 29
<211> LENGTH: 21
<212> TYPE: PRT
<213> ORGANISM: Artificial sequence
<220> FEATURE:
<223> OTHER INFORMATION: Synthetic peptide

<400> SEQUENCE: 29

Lys Glu Thr Trp Trp Glu Thr Trp Trp Thr Glu Trp Ser Gln Pro Lys
1               5                   10                  15

Lys Lys Arg Lys Val
            20


<210> SEQ ID NO 30
<211> LENGTH: 20
<212> TYPE: PRT
<213> ORGANISM: Artificial sequence
<220> FEATURE:
<223> OTHER INFORMATION: Synthetic peptide

<400> SEQUENCE: 30

Leu Lys Lys Leu Leu Lys Lys Leu Leu Lys Lys Leu Leu Lys Lys Leu
1               5                   10                  15

Leu Lys Lys Leu
            20


<210> SEQ ID NO 31
<211> LENGTH: 34
<212> TYPE: PRT
<213> ORGANISM: Artificial sequence
<220> FEATURE:
<223> OTHER INFORMATION: Synthetic peptide

<400> SEQUENCE: 31

Gln Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu


<210> SEQ ID NO 32
<211> LENGTH: 23
<212> TYPE: PRT
<213> ORGANISM: Artificial sequence
<220> FEATURE:
<223> OTHER INFORMATION: Synthetic peptide

<400> SEQUENCE: 32

Met Gly Leu Gly Leu His Leu Leu Val Leu Ala Ala Ala Leu Gln Gly
1               5                   10                  15

Ala Lys Ser Lys Arg Lys Val
            20


<210> SEQ ID NO 33
<211> LENGTH: 26
<212> TYPE: PRT
<213> ORGANISM: Artificial sequence
<220> FEATURE:
<223> OTHER INFORMATION: Synthetic peptide
```

<400> SEQUENCE: 33

Ala Ala Val Ala Leu Leu Pro Ala Val Leu Leu Ala Leu Leu Ala Pro
1 5 10 15

Ala Ala Ala Asn Tyr Lys Lys Pro Lys Leu
20 25

<210> SEQ ID NO 34
<211> LENGTH: 28
<212> TYPE: PRT
<213> ORGANISM: Artificial sequence
<220> FEATURE:
<223> OTHER INFORMATION: Synthetic peptide

<400> SEQUENCE: 34

Met Ala Asn Leu Gly Tyr Trp Leu Leu Ala Leu Phe Val Thr Met Trp
1 5 10 15

Thr Asp Val Gly Leu Cys Lys Lys Arg Pro Lys Pro
20 25

<210> SEQ ID NO 35
<211> LENGTH: 24
<212> TYPE: PRT
<213> ORGANISM: Artificial sequence
<220> FEATURE:
<223> OTHER INFORMATION: Synthetic peptide

<400> SEQUENCE: 35

Leu Gly Thr Tyr Thr Gln Asp Phe Asn Lys Phe His Thr Phe Pro Gln
1 5 10 15

Thr Ala Ile Gly Val Gly Ala Pro
20

<210> SEQ ID NO 36
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (24)..(24)
<223> OTHER INFORMATION: Xaa can be any naturally occurring amino acid

<400> SEQUENCE: 36

Asp Pro Lys Gly Asp Pro Lys Gly Val Thr Val Thr Val Thr Val Thr
1 5 10 15

Val Thr Gly Lys Gly Asp Pro Xaa Pro Asp
20 25

<210> SEQ ID NO 37
<211> LENGTH: 14
<212> TYPE: PRT
<213> ORGANISM: Artificial sequence
<220> FEATURE:
<223> OTHER INFORMATION: Synthetic peptide

<400> SEQUENCE: 37

Pro Pro Pro Pro Pro Pro Pro Pro Pro Pro Pro Pro Pro Pro
1 5 10

<210> SEQ ID NO 38
<211> LENGTH: 18
<212> TYPE: PRT
<213> ORGANISM: Artificial sequence
<220> FEATURE:

<223> OTHER INFORMATION: Synthetic peptide

<400> SEQUENCE: 38

```
Val Arg Leu Pro Pro Pro Val Arg Leu Pro Pro Pro Val Arg Leu Pro
1               5                   10                  15

Pro Pro
```

<210> SEQ ID NO 39
<211> LENGTH: 10
<212> TYPE: PRT
<213> ORGANISM: Artificial sequence
<220> FEATURE:
<223> OTHER INFORMATION: Synthetic peptide

<400> SEQUENCE: 39

```
Pro Arg Pro Leu Pro Pro Pro Arg Pro Gly
1               5                   10
```

<210> SEQ ID NO 40
<211> LENGTH: 30
<212> TYPE: PRT
<213> ORGANISM: Artificial sequence
<220> FEATURE:
<223> OTHER INFORMATION: Synthetic peptide

<400> SEQUENCE: 40

```
Ser Val Arg Arg Arg Pro Arg Pro Pro Tyr Leu Pro Arg Pro Arg Pro
1               5                   10                  15

Pro Pro Phe Phe Pro Pro Arg Leu Pro Pro Arg Ile Pro Pro
            20                  25                  30
```

<210> SEQ ID NO 41
<211> LENGTH: 21
<212> TYPE: PRT
<213> ORGANISM: Artificial sequence
<220> FEATURE:
<223> OTHER INFORMATION: Synthetic peptide

<400> SEQUENCE: 41

```
Thr Arg Ser Ser Arg Ala Gly Leu Gln Phe Pro Val Gly Arg Val His
1               5                   10                  15

Arg Leu Leu Arg Lys
            20
```

<210> SEQ ID NO 42
<211> LENGTH: 23
<212> TYPE: PRT
<213> ORGANISM: Artificial sequence
<220> FEATURE:
<223> OTHER INFORMATION: Synthetic peptide

<400> SEQUENCE: 42

```
Gly Ile Gly Lys Phe Leu His Ser Ala Lys Lys Phe Gly Lys Ala Phe
1               5                   10                  15

Val Gly Glu Ile Met Asn Ser
            20
```

<210> SEQ ID NO 43
<211> LENGTH: 37
<212> TYPE: PRT
<213> ORGANISM: Artificial sequence
<220> FEATURE:
<223> OTHER INFORMATION: Synthetic peptide

<400> SEQUENCE: 43

Lys Trp Lys Leu Phe Lys Lys Ile Glu Lys Val Gly Gln Asn Ile Arg
1 5 10 15

Asp Gly Ile Ile Lys Ala Gly Pro Ala Val Ala Val Val Gly Gln Ala
20 25 30

Thr Gln Ile Ala Lys
35

<210> SEQ ID NO 44
<211> LENGTH: 28
<212> TYPE: PRT
<213> ORGANISM: Artificial sequence
<220> FEATURE:
<223> OTHER INFORMATION: Synthetic peptide

<400> SEQUENCE: 44

Ala Leu Trp Met Thr Leu Leu Lys Lys Val Leu Lys Ala Ala Ala Lys
1 5 10 15

Ala Ala Leu Asn Ala Val Leu Val Gly Ala Asn Ala
20 25

<210> SEQ ID NO 45
<211> LENGTH: 26
<212> TYPE: PRT
<213> ORGANISM: Artificial sequence
<220> FEATURE:
<223> OTHER INFORMATION: Synthetic peptide

<400> SEQUENCE: 45

Gly Ile Gly Ala Val Leu Lys Val Leu Thr Thr Gly Leu Pro Ala Leu
1 5 10 15

Ile Ser Trp Ile Lys Arg Lys Arg Gln Gln
20 25

<210> SEQ ID NO 46
<211> LENGTH: 14
<212> TYPE: PRT
<213> ORGANISM: Artificial sequence
<220> FEATURE:
<223> OTHER INFORMATION: Synthetic peptide

<400> SEQUENCE: 46

Ile Asn Leu Lys Ala Leu Ala Ala Leu Ala Lys Lys Ile Leu
1 5 10

<210> SEQ ID NO 47
<211> LENGTH: 33
<212> TYPE: PRT
<213> ORGANISM: Artificial sequence
<220> FEATURE:
<223> OTHER INFORMATION: Synthetic peptide

<400> SEQUENCE: 47

Gly Phe Phe Ala Leu Ile Pro Lys Ile Ile Ser Ser Pro Leu Pro Lys
1 5 10 15

Thr Leu Leu Ser Ala Val Gly Ser Ala Leu Gly Gly Ser Gly Gly Gln
20 25 30

Glu

<210> SEQ ID NO 48
<211> LENGTH: 15
<212> TYPE: PRT
<213> ORGANISM: Artificial sequence
<220> FEATURE:

<223> OTHER INFORMATION: Synthetic peptide

<400> SEQUENCE: 48

```
Leu Ala Lys Trp Ala Leu Lys Gln Gly Phe Ala Lys Leu Lys Ser
1               5                   10                  15
```

<210> SEQ ID NO 49
<211> LENGTH: 27
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (23)..(23)
<223> OTHER INFORMATION: Xaa can be any naturally occurring amino acid

<400> SEQUENCE: 49

```
Ser Met Ala Gln Asp Ile Ile Ser Thr Ile Gly Asp Leu Val Lys Trp
1               5                   10                  15

Ile Ile Gln Thr Val Asn Xaa Phe Thr Lys Lys
            20                  25
```

<210> SEQ ID NO 50
<211> LENGTH: 41
<212> TYPE: PRT
<213> ORGANISM: Artificial sequence
<220> FEATURE:
<223> OTHER INFORMATION: Synthetic peptide

<400> SEQUENCE: 50

```
Leu Leu Gly Asp Phe Phe Arg Lys Ser Lys Glu Lys Ile Gly Lys Glu
1               5                   10                  15

Phe Lys Arg Ile Val Gln Arg Ile Lys Gln Arg Ile Lys Asp Phe Leu
            20                  25                  30

Ala Asn Leu Val Pro Arg Thr Glu Ser
        35                  40
```

<210> SEQ ID NO 51
<211> LENGTH: 18
<212> TYPE: PRT
<213> ORGANISM: Artificial sequence
<220> FEATURE:
<223> OTHER INFORMATION: Synthetic peptide

<400> SEQUENCE: 51

```
Pro Ala Trp Arg Lys Ala Phe Arg Trp Ala Trp Arg Met Leu Lys Lys
1               5                   10                  15

Ala Ala
```

<210> SEQ ID NO 52
<211> LENGTH: 18
<212> TYPE: PRT
<213> ORGANISM: Artificial sequence
<220> FEATURE:
<223> OTHER INFORMATION: Synthetic peptide

<400> SEQUENCE: 52

```
Lys Leu Lys Leu Lys Leu Lys Leu Lys Leu Lys Leu Lys Leu Lys Leu
1               5                   10                  15

Lys Leu
```

<210> SEQ ID NO 53
<211> LENGTH: 20

<212> TYPE: PRT
<213> ORGANISM: Artificial sequence
<220> FEATURE:
<223> OTHER INFORMATION: Synthetic peptide

<400> SEQUENCE: 53

Pro Gly Lys Lys Thr Arg Gly Arg Val Lys Ile Lys Met Glu Phe Ile
1 5 10 15

Asp Asn Lys Leu
20

<210> SEQ ID NO 54
<211> LENGTH: 20
<212> TYPE: PRT
<213> ORGANISM: Artificial sequence
<220> FEATURE:
<223> OTHER INFORMATION: Synthetic peptide

<400> SEQUENCE: 54

Pro Gly Lys Lys Thr Ala Ala Ala Val Lys Ile Lys Met Glu Phe Ile
1 5 10 15

Asp Asn Lys Leu
20

<210> SEQ ID NO 55
<211> LENGTH: 20
<212> TYPE: PRT
<213> ORGANISM: Artificial sequence
<220> FEATURE:
<223> OTHER INFORMATION: Synthetic peptide

<400> SEQUENCE: 55

Pro Gly Lys Lys Thr Arg Gly Arg Ala Ala Ala Lys Met Glu Phe Ile
1 5 10 15

Asp Asn Lys Leu
20

<210> SEQ ID NO 56
<211> LENGTH: 20
<212> TYPE: PRT
<213> ORGANISM: Artificial sequence
<220> FEATURE:
<223> OTHER INFORMATION: Synthetic peptide

<400> SEQUENCE: 56

Pro Gly Lys Lys Thr Arg Gly Arg Val Lys Ile Ala Ala Ala Phe Ile
1 5 10 15

Asp Asn Lys Leu
20

<210> SEQ ID NO 57
<211> LENGTH: 20
<212> TYPE: PRT
<213> ORGANISM: Artificial sequence
<220> FEATURE:
<223> OTHER INFORMATION: Synthetic peptide

<400> SEQUENCE: 57

Pro Gly Lys Lys Thr Arg Gly Arg Val Lys Ile Lys Met Glu Ala Ala
1 5 10 15

Ala Asn Lys Leu
20

<210> SEQ ID NO 58

-continued

```
<211> LENGTH: 20
<212> TYPE: PRT
<213> ORGANISM: Artificial sequence
<220> FEATURE:
<223> OTHER INFORMATION: Synthetic peptide

<400> SEQUENCE: 58

Pro Gly Lys Lys Thr Arg Gly Arg Val Lys Ile Lys Met Glu Phe Ile
1               5                   10                  15

Asp Ala Ala Ala
            20
```